(12) United States Patent
Barrett et al.

(10) Patent No.: US 11,801,136 B2
(45) Date of Patent: Oct. 31, 2023

(54) DELIVERY SYSTEM HAVING AN INTEGRAL CENTERING MECHANISM FOR POSITIONING A VALVE PROSTHESIS IN SITU

(71) Applicant: Medtronic Vascular, Inc., Santa Rosa, CA (US)

(72) Inventors: Donna Barrett, Ballybrit (IE); Kieran Cunningham, Ballybrit (IE); Frank Harewood, Ballybrit (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 0 days.

(21) Appl. No.: 17/675,033

(22) Filed: Feb. 18, 2022

(65) Prior Publication Data

US 2022/0175528 A1    Jun. 9, 2022

Related U.S. Application Data

(60) Continuation of application No. 16/601,642, filed on Oct. 15, 2019, now Pat. No. 11,278,407, which is a division of application No. 15/000,378, filed on Jan. 19, 2016, now Pat. No. 10,478,297.

(60) Provisional application No. 62/108,192, filed on Jan. 27, 2015.

(51) Int. Cl.
*A61F 2/24* (2006.01)

(52) U.S. Cl.
CPC .................................. *A61F 2/2436* (2013.01)

(58) Field of Classification Search
CPC ...... A61F 2/2436; A61F 2/2427; A61F 2/243; A61F 2/2439; A61M 2025/1047; A61B 2017/22034; A61B 2017/2212
See application file for complete search history.

(56) References Cited

U.S. PATENT DOCUMENTS

| 4,909,252 A | 3/1990 | Goldberger |
| 5,840,067 A | 11/1998 | Berguer et al. |
| 6,629,534 B1 | 10/2003 | St. Goar et al. |

(Continued)

OTHER PUBLICATIONS

The International Search Report and The Written Opinion of The International Searching Authority issued in International Application No. PCT/US2016/015157 dated Apr. 26, 2016.

*Primary Examiner* — Majid Jamialahmadi
(74) *Attorney, Agent, or Firm* — MEDLER FERRO WOODHOUSE & MILLS PLLC

(57) ABSTRACT

Embodiments hereof relate to a delivery system for a transcatheter valve prosthesis, the delivery system having an integral centering mechanism to circumferentially center both the delivery system and the valve prosthesis within a vessel at the target implantation site. The centering mechanism may include expandable wings that may be selectively aligned with openings formed through a sidewall of an outer shaft of the delivery system, a coiled wing that may be selectively exposed through an opening formed through a sidewall of an outer shaft of the delivery system, a plurality of elongated filaments extending through a plurality of lumens of an outermost shaft of the delivery system that may be selectively deployed or expanded, an outer shaft that includes at least one pre-formed deflection segment formed thereon, a tool having a deployable lever arm, and/or a plurality of loops deployable via simultaneous longitudinal and rotational movement.

15 Claims, 23 Drawing Sheets

(56) References Cited

U.S. PATENT DOCUMENTS

| | | |
|---|---|---|
| 8,142,492 B2 | 3/2012 | Forster et al. |
| 8,454,686 B2 | 6/2013 | Alkhatib |
| 8,715,337 B2 | 5/2014 | Chuter |
| 8,961,595 B2 | 2/2015 | Alkhatib |
| 9,017,399 B2 | 4/2015 | Gross et al. |
| 9,603,705 B2 | 3/2017 | Alkhatib |
| 2004/0003819 A1 | 1/2004 | St. Goar et al. |
| 2004/0225354 A1 | 11/2004 | Allen et al. |
| 2005/0154400 A1 | 7/2005 | Kato et al. |
| 2007/0088431 A1 | 4/2007 | Bourang et al. |
| 2008/0009746 A1 | 1/2008 | Forster et al. |
| 2008/0147160 A1 | 6/2008 | Ghione et al. |
| 2008/0221384 A1 | 9/2008 | Sing et al. |
| 2010/0249915 A1 | 9/2010 | Zhang |
| 2010/0280589 A1 | 11/2010 | Styrc |
| 2011/0245911 A1 | 10/2011 | Quill et al. |
| 2011/0245917 A1 | 10/2011 | Savage et al. |
| 2011/0251675 A1 | 10/2011 | Dwork et al. |
| 2011/0251681 A1 | 10/2011 | Shipley et al. |
| 2011/0251682 A1 | 10/2011 | Murray, III |
| 2011/0264200 A1* | 10/2011 | Tran ............... A61F 2/2436 623/2.11 |
| 2011/0264202 A1 | 10/2011 | Murray, III |
| 2012/0209375 A1 | 8/2012 | Madrid et al. |
| 2013/0304200 A1 | 11/2013 | Mclean et al. |
| 2013/0325101 A1 | 12/2013 | Goeiz et al. |
| 2013/0331929 A1 | 12/2013 | Mitra et al. |
| 2014/0018912 A1 | 1/2014 | Delaloye et al. |
| 2014/0088680 A1 | 3/2014 | Costello et al. |
| 2014/0194981 A1 | 7/2014 | Menk et al. |
| 2014/0257248 A1 | 9/2014 | Millett |
| 2014/0371844 A1 | 12/2014 | Dale et al. |
| 2015/0018944 A1 | 1/2015 | O'Connell et al. |
| 2015/0209136 A1 | 7/2015 | Braido et al. |
| 2015/0250991 A1 | 9/2015 | Silvestro |
| 2017/0189180 A1 | 7/2017 | Alkhatib |
| 2017/0189181 A1 | 7/2017 | Alkhatib et al. |
| 2017/0209261 A1 | 7/2017 | Bortlein et al. |
| 2017/0252154 A1 | 9/2017 | Tubishevitz et al. |
| 2017/0290661 A1 | 10/2017 | Segesser et al. |
| 2017/0340438 A1 | 11/2017 | Salahieh et al. |

* cited by examiner

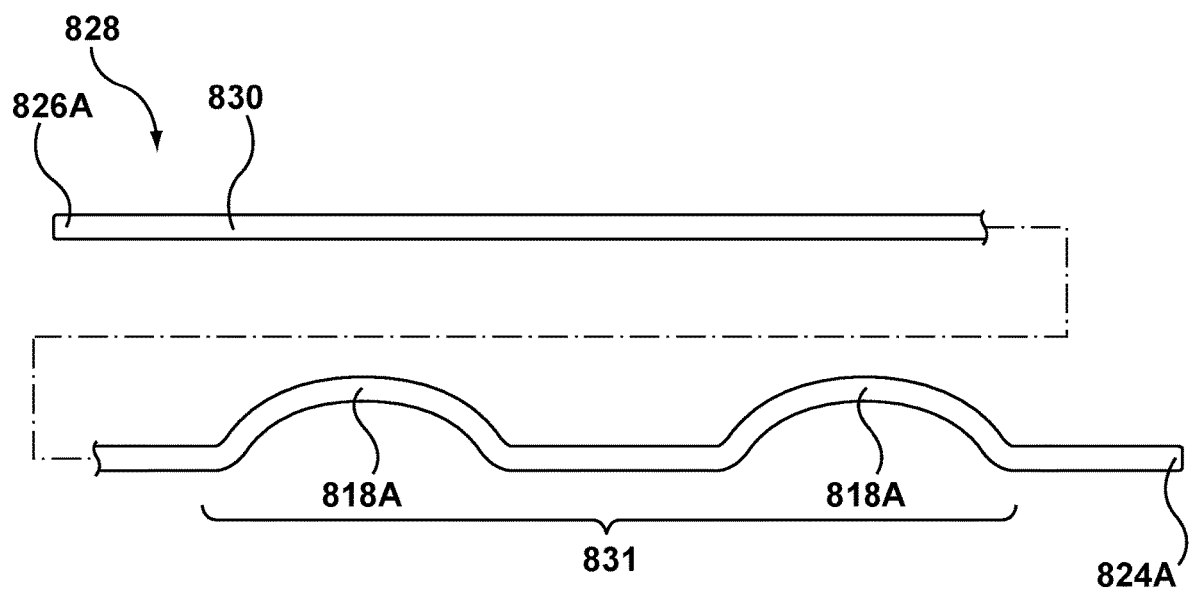
FIG. 8
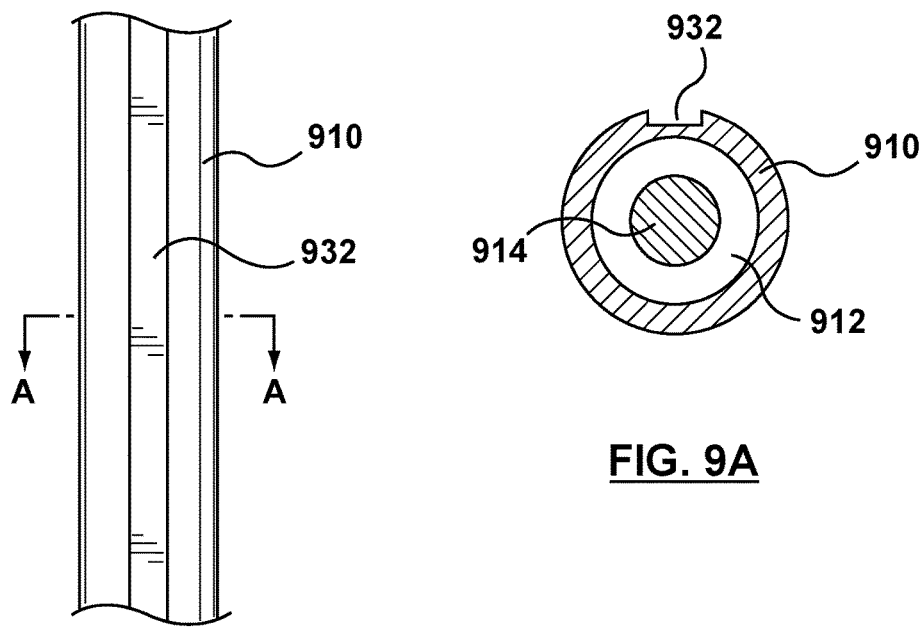
FIG. 9
FIG. 9A

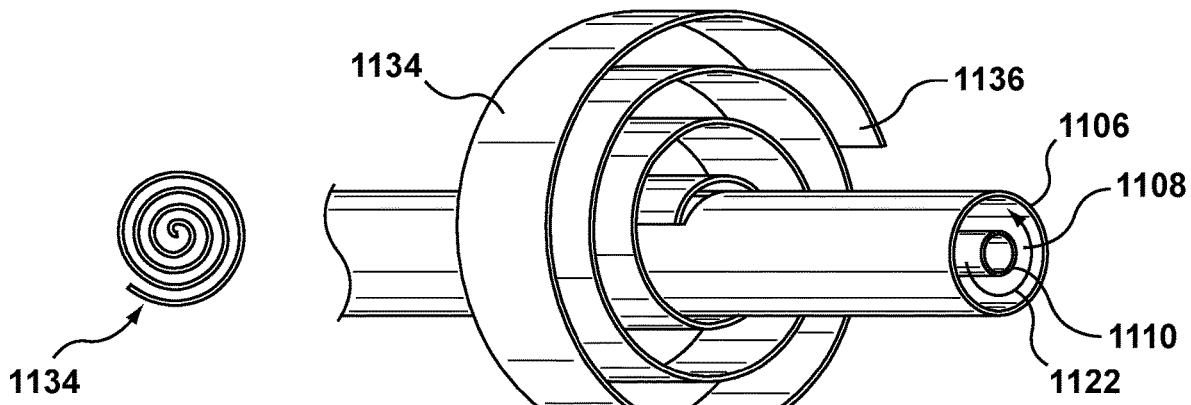
FIG. 13
FIG. 14
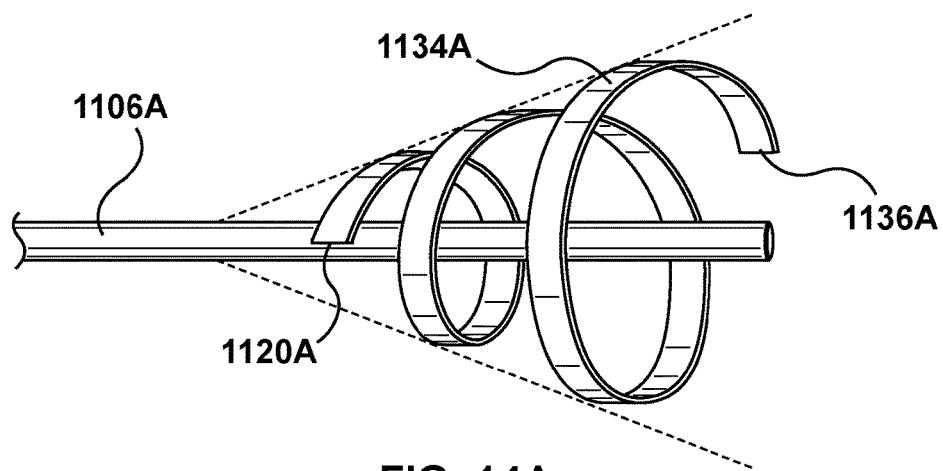
FIG. 14A
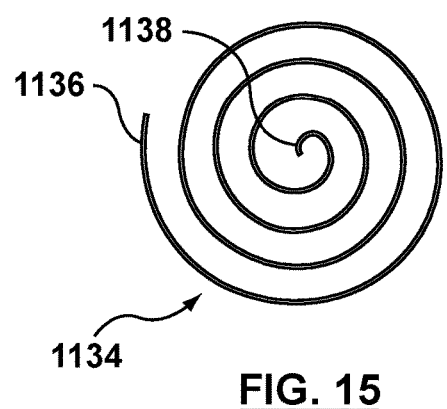
FIG. 15

DELIVERY SYSTEM HAVING AN INTEGRAL CENTERING MECHANISM FOR POSITIONING A VALVE PROSTHESIS IN SITU

CROSS-REFERENCE TO RELATED APPLICATIONS

This application is a continuation of U.S. application Ser. No. 16/601,642, filed Oct. 15, 2019, now allowed, which is a Divisional of U.S. application Ser. No. 15/000,378 filed Jan. 19, 2016, now U.S. Pat. No. 10,478,297, which claims the benefit of U.S. Provisional Patent Application Ser. No. 62/108,192, filed Jan. 27, 2015, the disclosure of each of which is hereby incorporated by reference in its entirety for all purposes.

FIELD OF THE INVENTION

The invention relates to a delivery system and more particularly to a delivery system having an integral centering mechanism for positioning a valve prosthesis in situ.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent or scaffold structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by compressing onto a balloon catheter or by being contained within a sheath component of a delivery system, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Pat. No. 8,721,713, both filed by Tower et al., each of which is incorporated by reference herein in its entirety.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. More particularly, for example, a prosthesis that is positioned too deep relative to the native annulus or placed unevenly within the native annulus in terms of depth may cause conduction disturbances. In another example, if a prosthesis is not circumferentially centered relative to the native annulus, the deployed prosthesis may dislodge from the implantation site and/or undesirable paravalvular leakage and/or regurgitation may occur. Thus, it is imperative that the prosthesis be accurately located relative to the native annulus prior to full deployment of the prosthesis.

Embodiments hereof are directed to a delivery system for a transcatheter valve prosthesis having an integral centering mechanism for positioning a valve prosthesis in situ to address one or more of the afore-mentioned complications.

BRIEF SUMMARY OF THE INVENTION

Embodiments hereof relate to delivery systems for a valve prosthesis configured for delivery within a vasculature. In an embodiment hereof, the delivery system includes an outer shaft defining a lumen and at least two windows formed through a sidewall thereof and an inner shaft concentrically disposed within the lumen of the outer shaft. The inner shaft has a distal portion being configured to receive the valve prosthesis thereon. The delivery system also includes at least one centering mechanism including at least two wings. A first end of each wing is attached to the inner shaft and a second end is free to slide over the inner shaft. When the centering mechanism is in a delivery configuration each wing is offset from one of the windows of the outer shaft and has a straightened profile that is enclosed between the outer and inner shafts. When the centering mechanism is in an expanded configuration each wing has a curved, bowed profile and is aligned with and radially extends through one of the windows of the outer shaft.

In another embodiment hereof, the delivery system includes an outer shaft defining a lumen and at least one window formed through a sidewall thereof and an inner shaft concentrically disposed within the lumen of the outer shaft. The inner shaft has a distal portion being configured to receive the valve prosthesis thereon, and the inner shaft is rotatable with respect to the outer shaft. The delivery system also includes at least one centering mechanism including at least one coiled wing. A first end of the coiled wing is attached to the inner shaft and a second end is unattached to inner shaft. When the centering mechanism is in a delivery configuration the coiled wing has a series of windings that extend around the inner shaft such that each winding is enclosed between the outer and inner shafts. When the centering mechanism is in an expanded configuration the coiled wing extends through the window of the outer shaft and has a series of windings that extend around the outer shaft.

In another embodiment hereof, the delivery system includes an outermost shaft defining a central lumen and defining a plurality of lumens in a sidewall thereof, a retractable outer shaft concentrically disposed within the central lumen of the outermost shaft, and an inner shaft concentrically disposed within a lumen defined by the outer shaft. The inner shaft has a distal portion being configured to receive the valve prosthesis thereon. The delivery system also includes a plurality of elongated filaments slidingly positioned within the plurality of lumens of the outermost shaft. Each filament has at least a distal portion formed from a self-expanding material. When each elongated filament is in a delivery configuration the distal portion of each elongated filament has a straightened profile that is enclosed within one of the lumens in the sidewall of the outermost shaft. When each elongated filament is in an expanded configuration the distal portion of each elongated filament has a curved, bowed profile and extends out of a distal end of the outermost shaft.

In another embodiment hereof, the delivery system includes an outermost shaft defining a central lumen and defining a plurality of lumens in a sidewall thereof, a retractable outer shaft concentrically disposed within the central lumen of the outermost shaft, and an inner shaft concentrically disposed within a lumen defined by the outer shaft. The inner shaft has a distal portion being configured to receive the valve prosthesis thereon. The delivery system also includes a plurality of elongated filaments slidingly positioned within the plurality of lumens of the outermost shaft. A distal end of each elongated filament is attached to an outer surface of the outer shaft. When each elongated filament is in a delivery configuration a distal portion of each elongated filament has a straightened profile that is flush against the outer surface of the outer shaft. When each elongated filament is in an expanded configuration the distal portion of each elongated filament has a curved, bowed profile radially spaced apart from the outer surface of the outer shaft.

In another embodiment hereof, the delivery system includes an outer shaft defining a lumen, the outer shaft including at least one pre-formed deflection segment formed thereon. The deflection segment has a curved, bowed profile with respect to the remaining length of the outer shaft. The delivery system also includes an inner shaft concentrically disposed within the lumen of the outer shaft. The inner shaft has a distal portion being configured to receive the valve prosthesis thereon. The outer shaft is sufficiently flexible to deform into a substantially straight configuration when percutaneously introduced into a vasculature.

Another embodiment hereof relates to a tool for use with a delivery system for a valve prosthesis configured for delivery within a vasculature. The tool includes a shaft component defining a lumen, the shaft component having a proximal end and a distal end. A handle is coupled to the proximal end of the shaft component and a lever arm is coupled to the distal end of the shaft component. The level arm has a first end attached to an outer surface of the shaft component. When the lever arm is in a delivery configuration the second end of the lever arm is detachably coupled to the outer surface of the shaft component and the lever arm has a straightened profile that is flush against the outer surface of the shaft component. When the lever arm is in an expanded configuration the second end of the lever arm is detached from the shaft component and the second end of the lever arm self-expands radially away from the shaft component such that the lever arm forms an acute angle with respect to the outer surface of the shaft component.

In another embodiment hereof, the delivery system includes an outermost shaft defining a central lumen, an outer shaft concentrically disposed within the central lumen of the outermost shaft, and an inner shaft concentrically disposed within a lumen defined by the outer shaft. The outer shaft is rotatable and slidable relative to the outermost shaft. The inner shaft has a distal portion being configured to receive the valve prosthesis thereon. The delivery system also includes a plurality of deployable loops, a first end of each loop being attached to a distal end of the outermost shaft and a second end of each loop being attached to the outer shaft. When each loop is in a delivery configuration the loop has a straightened profile that is flush against the outer surface of the outer shaft. When each loop is in an expanded configuration the loop has a curved, bowed profile radially spaced apart from the outer surface of the outer shaft and also spirals with respect to the outer shaft.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 8 is a side view of a centering mechanism according to another embodiment hereof, the centering mechanism being removed from the delivery system for illustrative purposes only, wherein the centering mechanism is in a deployed or expanded configuration.

FIG. 9 is a side view of a portion of a delivery system according to another embodiment hereof, wherein the delivery system includes grooves to assist in deployment of a centering mechanism.

FIG. 9A is a cross-sectional view taken along line A-A of FIG. 9.

FIG. 13 is a side view of the centering mechanism of FIG. 12, the centering mechanism being removed from the delivery system for illustrative purposes only, wherein the centering mechanism is in a delivery or unexpanded configuration.

FIG. 14 is a perspective view of a portion of the delivery system of FIG. 11, wherein the centering mechanism is in a deployed or expanded configuration.

FIG. 14A is a perspective view of a portion of the delivery system of FIG. 12A, wherein the centering mechanism is in a deployed or expanded configuration.

FIG. 15 is a side view of the centering mechanism of FIG. 14, the centering mechanism being removed from the delivery system for illustrative purposes only, wherein the centering mechanism is in a deployed or expanded configuration.

DETAILED DESCRIPTION OF THE INVENTION

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers. The term "substantially straight" and/or "straightened" is used in the following description and is intended to convey that the structures are linearly shaped or formed as a line within a tolerance of 5%.

The following detailed description is merely exemplary in nature and is not intended to limit the invention or the application and uses of the invention. Although the description of embodiments hereof are in the context of delivery systems for delivering a prosthetic heart valve within a native aortic valve, the delivery systems of the invention can also be used in other areas of the body, such as for delivering a prosthetic heart valve within a native mitral valve, for delivering a prosthetic heart valve within a native pulmonic valve, for delivering a prosthetic heart valve within a native tricuspid valve, for delivering a venous valve, or for delivering a prosthetic heart valve within a failed previously-implanted prosthesis. Furthermore, there is no intention to be bound by any expressed or implied theory presented in the preceding technical field, background, brief summary or the following detailed description.

Figures 1, 1A:
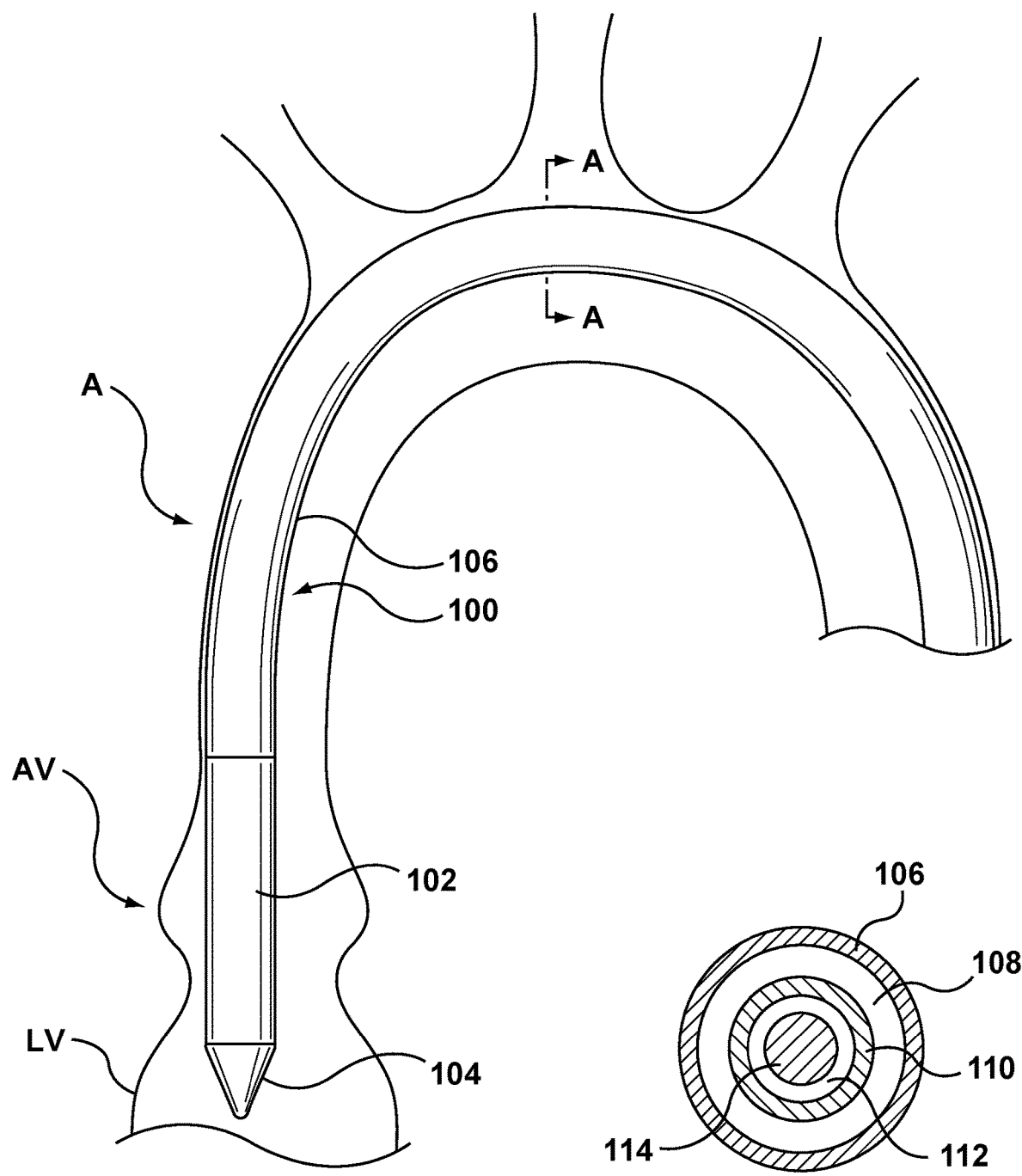
FIG. 1 is an illustration of a delivery system in situ.
FIG. 1A is a cross-sectional view taken along line A-A of FIG. 1.

FIGS. 1-1A illustrate a delivery system 100 that is configured for endoluminal transcatheter repair/replacement of a defective heart valve. Delivery system 100 is depicted in a delivery configuration in FIG. 1 with a prosthetic heart valve (not shown) loaded within a distal capsule section 102 of the delivery system. As shown in FIG. 1A, delivery system 100 also includes a tubular outer shaft 106 defining a lumen 108 there-through and a tubular inner shaft 110 defining a lumen 112 there-through. A distal tip 104 is coupled to a distal end of inner shaft 110. Inner shaft 110 is concentrically disposed within lumen 108 of outer shaft 106, and lumen 112 of inner shaft 110 may be sized to slidingly receive a guidewire 114 such that delivery system 100 may be tracked over the guidewire during delivery of the prosthetic heart valve. In the delivery configuration of FIG. 1, distal capsule section 102 is disposed over the prosthetic heart valve to compressively retain the prosthetic heart valve in crimped engagement with inner shaft 110. Delivery system 100 may be one of, but is not limited to, the delivery systems described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety.

Although the prosthetic heart is not shown, it will be understood by those of ordinary skill in the art that the prosthetic heart valve includes a stent frame maintaining a valve structure (tissue or synthetic) within the stent frame, the stent frame being biased in its expanded configuration and being collapsible to a compressed delivery arrangement for loading within delivery system 100. The stent frame is constructed to self-deploy or self-expand when released from delivery system 100. In an embodiment, a prosthetic heart valve useful with embodiments hereof can be a prosthetic heart valve as disclosed in U.S. Pat. Appl. Pub. No. 2008/0071361 to Tuval et al., which is incorporated by reference herein in its entirety. Other non-limiting examples of transcatheter heart valve prostheses useful with systems and methods of the present disclosure are described in U.S. Pat. Appl. Pub. No. 2006/0265056 to Nguyen et al., U.S. Pat. Appl. Pub. No. 2007/0239266 to Birdsall, and U.S. Pat. Appl. Pub. No. 2007/0239269 to Dolan et al., each of which is incorporated by reference herein in its entirety.

As shown in FIG. 1, in accordance with techniques known in the field of interventional cardiology and/or interventional radiology, delivery system 100 is transluminally advanced in a retrograde approach through the vasculature to the treatment site, which in this instance is a target diseased native aortic valve AV that extends between a patient's left ventricle LV and a patient's aorta A. Delivery of delivery system 100 to the native aortic valve AV is accomplished via a percutaneous transfemoral approach in which the delivery system is tracked through the femoral artery, up the aorta and around the aortic arch in order to access the native aortic valve AV. Delivery system 100 may also be positioned within the desired area of the heart via different delivery methods known in the art for accessing heart valves. During delivery, the prosthetic heart valve remains compressed within distal capsule section 102 of the delivery system. Delivery system 100 is advanced until distal tip 104 is distal to the native aortic valve AV and disposed within the left ventricle LV as shown in FIG. 1. As delivery system 100 is tracked to the native aortic valve AV, the delivery system may abut against or hug the vessel wall as shown in FIG. 1, thereby resulting in a non-centered position in the aorta A and in the native aortic valve AV. As described in the background section hereof, proper positioning of the delivery system and prosthetic heart valve is required in order to successfully implant the prosthetic heart valve against the native annulus. If the prosthesis is incorrectly positioned relative to the native annulus, the deployed device can leak and dislodge from the native valve implantation site.

Embodiments hereof are directed to a delivery system for a transcatheter valve prosthesis, the delivery system having an integral centering mechanism for positioning the valve prosthesis in situ such that both the delivery system and the valve prosthesis are circumferentially centered in a vessel at the target implantation site, such as for example an aorta A and a native aortic valve AV. As used herein, "circumferentially centered" and/or "circumferentially center" include a delivery system having a distal portion thereof that is placed or situated in the center of a body lumen such that a centerpoint of the distal portion of the delivery system is equidistant to the vessel wall of the body lumen within a tolerance of 10% of the mean lumen diameter of the body lumen. As used herein, "lumen diameter" for a circular body lumen is the diameter of the circular lumen, "lumen diameter" for an eccentric or non-circular body lumen is the diameter of a circular lumen with an equivalent perimeter length, and "lumen diameter" for an oval body lumen is the average of the major and minor diameters of the oval lumen. The integral centering mechanisms described herein prevent the delivery system from abutting against or hugging the vessel wall around curvatures thereof as described above with respect to FIG. 1. As such, the integral centering mechanisms described herein allow a delivery system to self-center itself without the requirement that the user steer the delivery system to the center of the body lumen. In addition, the integral centering mechanisms described herein may be utilized at any time during the delivery process. For example, although described herein primarily with respect to circumferentially centering the delivery system and valve prosthesis after the distal portion of the delivery system is positioned at the target native valve site but prior to deployment of the valve prosthesis, the integral centering mechanisms described herein may be utilized before the distal portion of the delivery system is positioned at the target native valve site to push or deflect the delivery system off a vessel wall while the delivery system is being tracked to the target native valve site.

Figure 2:
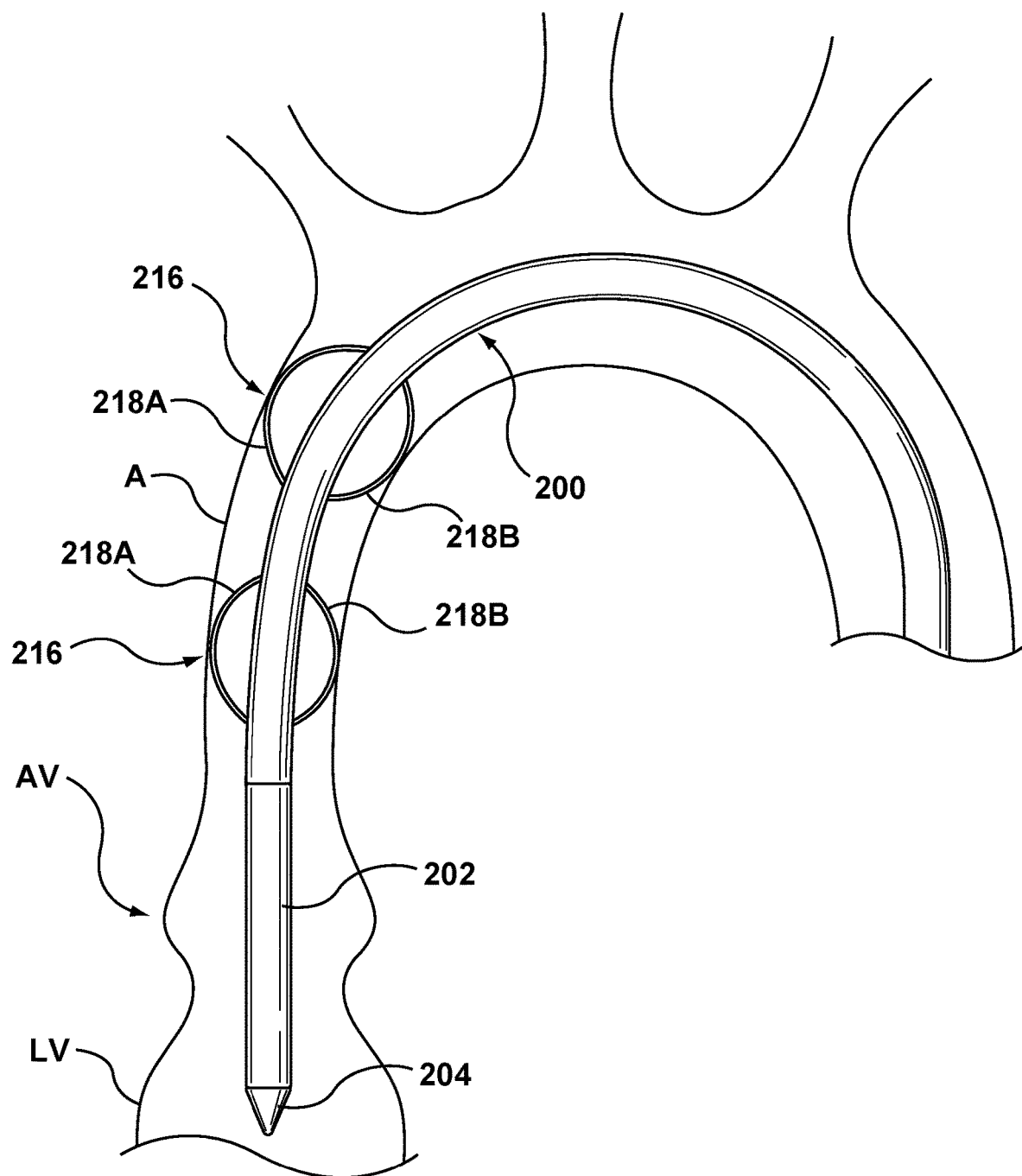
FIG. 2 is an illustration of a delivery system having an integral centering mechanism according to an embodiment hereof in situ, wherein the centering mechanism is in a deployed or expanded configuration.

With reference to FIG. 2, a delivery system 200 is configured for endoluminal transcatheter repair/replacement of a defective heart valve and includes two, longitudinally spaced apart integral centering mechanisms 216. In FIG. 2, delivery system 200 is depicted in situ, with centering mechanism 216 in a deployed or expanded configuration and a prosthetic heart valve (not shown) in a delivery or compressed configuration in which the prosthetic heart valve is loaded within a distal capsule section 202 of the delivery system. Although delivery system 200 is shown with two centering mechanisms 216 at longitudinally spaced-apart locations, delivery system 200 may include only one centering mechanism or may include more than two centering mechanisms at longitudinally spaced-apart locations along delivery system 200. Centering mechanisms 216 are positioned proximal to distal capsule section 202, and are positioned to deploy within the aorta A in order to center delivery system 200 and the prosthetic heart valve contained therein in the aorta A and in the native aortic valve AV.

Figure 3:
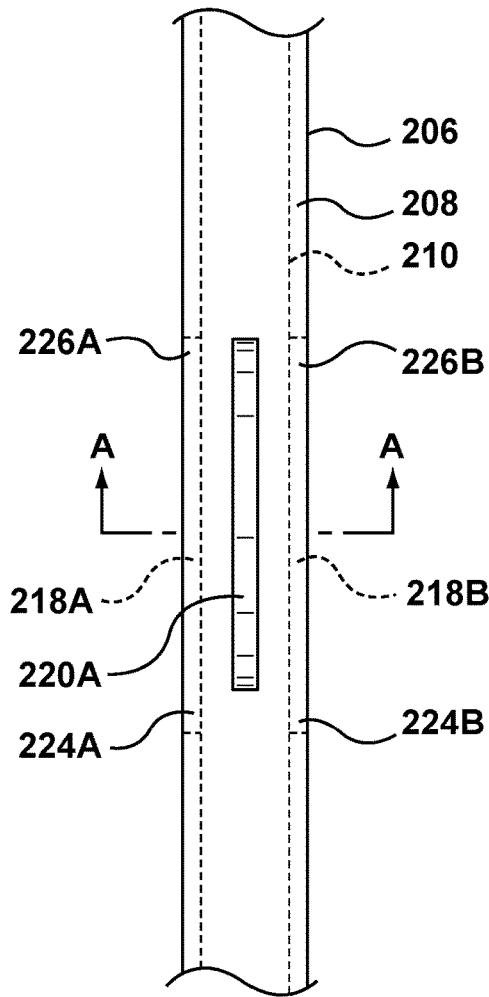
FIG. 3 is a side view of a portion of the delivery system of FIG. 2, wherein the centering mechanism is in a delivery or unexpanded configuration.
Figure 3A:
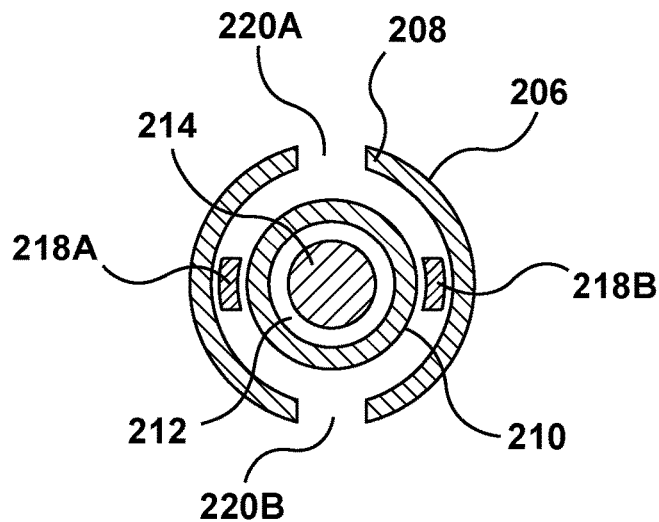
FIG. 3A is a cross-sectional view taken along line A-A of FIG. 3.

Similar to delivery system 100, as best shown on FIG. 3A, delivery system 200 includes a tubular outer shaft 206 defining a lumen 208 there-through and a tubular inner shaft 210 defining a lumen 212 there-through. A distal tip 204 (see FIG. 2) is coupled to a distal end of inner shaft 210. Inner shaft 210 is concentrically disposed within lumen 208 of outer shaft 206, and lumen 212 of inner shaft 210 may be sized to slidingly receive a guidewire 214 such that delivery system 200 may be tracked over the guidewire during delivery of the prosthetic heart valve.

Each centering mechanism 216 includes at least two expandable arms or wings 218A, 218B that, when expanded or deployed, are configured to deflect off of the vessel wall, i.e., aorta A, in order to push delivery system 200 away from the walls of the vessel and circumferentially center the delivery system within the vessel for a more successful prosthetic valve deployment. Each wing 218A, 218B is an individual or separate flat or ribbon-like element that is formed from a self-expanding material and shape-set in the deployed or expanded configuration shown in FIG. 2. In centering mechanism 216 is in the expanded or deployed configuration, each wing 218A, 218B is curved or arched such that each wing bows or bulges radially outward with respect to outer shaft 206. Stated another way, when the centering mechanism is in an expanded configuration, each wing 218A, 218B has a curved, bowed profile.

During delivery of delivery system 200, each wing 218A, 218B is collapsed or compressed into a delivery configuration in which each wing is enclosed or housed between outer shaft 206 and inner shaft 210 of the delivery system. More particularly, FIG. 3 and FIG. 3A illustrate a portion of delivery system 200, with wings 218A, 218B compressed into a delivery configuration. Each wing 218A has a first end 226A that is attached or anchored to inner shaft 210 and a second or opposing end 224A that is unattached so that the second end is free to slide over inner shaft 210 for deployment and recapture as will be explained in more detail herein. Similarly, each wing 218B has a first end 226B that is attached or anchored to inner shaft 210 and a second or opposing end 224B that is unattached so that the second end is free to slide over inner shaft 210 for deployment and recapture. First ends 226A, 226B of wings 218A, 218B, respectively, are attached to inner shaft 210 via bonding or adhesive. When compressed or collapsed, wings 218A, 218B extend between outer shaft 206 and inner shaft 210 as best shown in FIG. 3A, within lumen 208 of outer shaft 206, and thus advantageously do not increase the outer diameter or profile of delivery system 200. Outer shaft 206 includes openings or windows 220A, 220B formed through a sidewall thereof at circumferentially opposing positions. Openings or windows 220A, 220B are longitudinally aligned with wings 218A, 218B. However, when compressed or collapsed, openings or windows 220A, 220B circumferentially offset or not aligned with wings 218A, 218B such that the wings are contained within outer shaft 206. Stated another way, when centering mechanism 216 is in a delivery configuration, wings 218A, 218B are offset from windows 220A, 220B, respectively, each wing 218A, 218B has a straightened profile that is enclosed between the outer and inner shafts.

Figure 4:
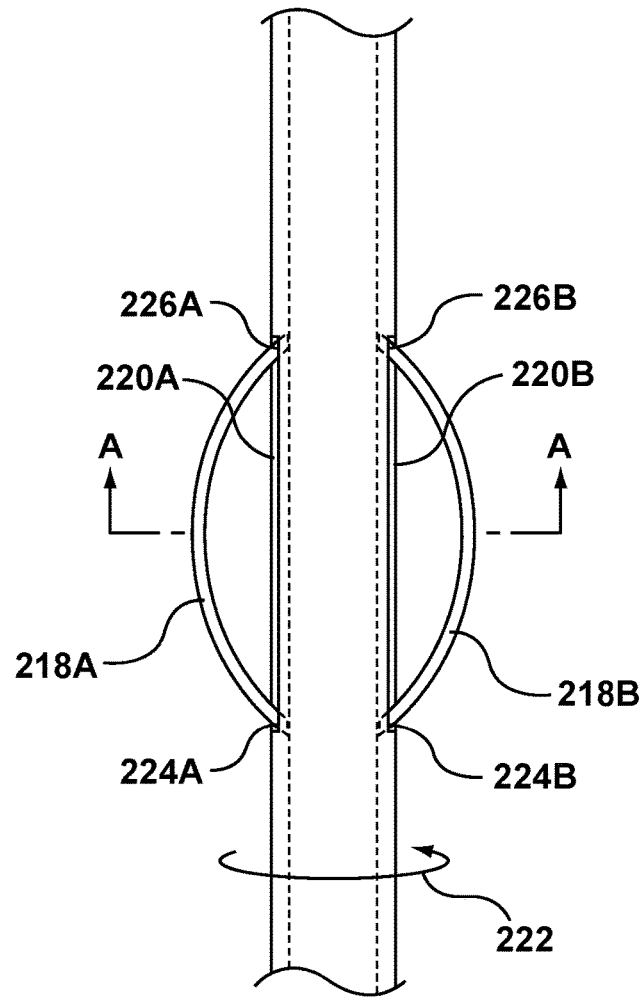
FIG. 4 is a side view of a portion of the delivery system of FIG. 2, wherein the centering mechanism is in a deployed or expanded configuration.
Figure 4A:
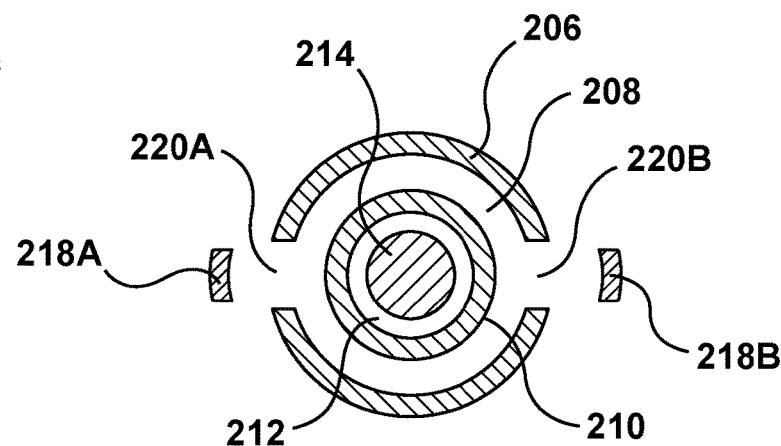
FIG. 4A is a cross-sectional view taken along line A-A of FIG. 4.

When it is desired to deploy or expand centering mechanisms 216, outer shaft 206 is rotated or turned relative to inner shaft 210 as indicated by directional arrow 222 on FIG. 4 in order to circumferentially align windows 220A, 220B with wings 218A, 218B. Once the windows are aligned with the wings, wings 218A, 218B are exposed and permitted to self-expand. More particularly, unattached or free second ends 224A, 224B of wings 218A, 218B, respectively, slide over inner shaft 210 in a proximal direction towards attached or anchored first ends 226A, 226B of wings 218A, 218B, respectively. Wings 218A, 218B resume their shape-set deployed or expanded configuration when permitted to radially expand through windows 220A, 220B. In the embodiment shown in FIGS. 4 and 4A, outer shaft 206 is rotated approximately 90 degrees in order to circumferentially align windows 220A, 220B with wings 218A, 218B. The degree or amount of rotation that is required may vary according to application including rotation angles between 10 and 90 ninety degrees. In addition, although described with second ends 224A, 224B of wings 218A, 218B, respectively, being unattached or free to slide in a proximal direction over inner shaft 210, in another embodiment hereof (not shown) first ends 226A, 226B of wings 218A, 218B, respectively, may alternatively be unattached or free to slide in a distal direction over inner shaft 210 when wings 218A, 218B expand or deploy through windows 220A, 220B while the second ends of the wings are attached or anchored to the inner shaft.

Centering mechanisms 216 need only be deployed if desired by the user. For example, if fluoroscopy reveals that delivery system 200 is circumferentially centered within the aorta A and in the native aortic valve AV without deployment of centering mechanisms 216, wings 218A, 218B may remain housed or contained within the delivery system throughout the delivery process. However, if fluoroscopy reveals that delivery system 200 is hugging or clinging to the vessel wall, centering mechanisms 216 may be selectively deployed in order to deflect or push delivery system 200 off the vessel wall. Centering mechanisms 216 are preferably expanded or deployed prior to deployment of the prosthetic heart valve, and centering mechanisms 216 may remain deployed or expanded during deployment of the prosthetic heart valve or may be retracted or recaptured prior to deployment of the prosthetic heart valve. In order to retract or recapture wings 218A, 218B, outer shaft 206 is rotated in the opposite direction from directional arrow 222 such that wings 218A, 218B are no longer circumferentially aligned with windows 220A, 220B. Unattached or free second ends 224A, 224B of wings 218A, 218B, respectively, slide over inner shaft 210 in a distal direction away from attached or anchored first ends 226A, 226B of wings 218A, 218B, respectively, such that wings 218A, 218B collapse and are again contained or housed within outer shaft 206 in a delivery configuration described above with respect to FIGS. 3 and 3A.

Figure 5:
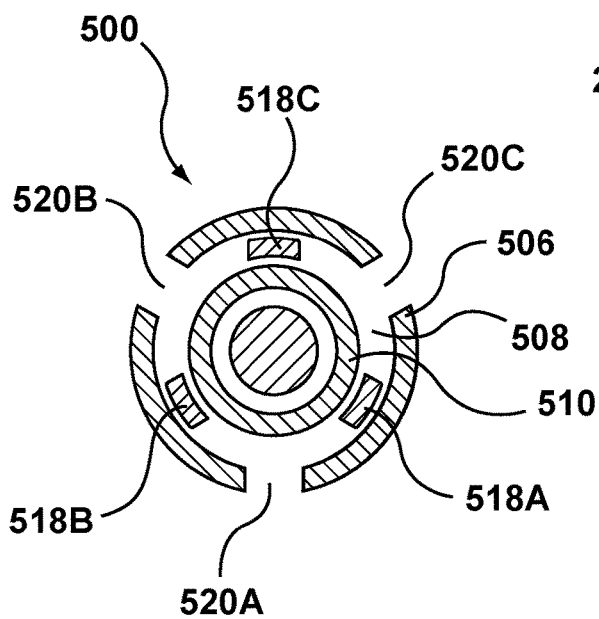
FIG. 5 is a cross-sectional view of a delivery system having an integral centering mechanism according to another embodiment hereof, wherein the centering mechanism includes three circumferentially spaced wings and the centering mechanism is in a delivery or unexpanded configuration.

In another embodiment hereof, each centering mechanism may include more than two opposing wings. For example, in the embodiment of FIG. 5, a centering mechanism having three circumferentially spaced wings 518A, 518B, 518C is shown in a delivery configuration in which each wing is enclosed or housed within a lumen 508 between an outer shaft 506 and inner shaft 510 of a delivery system 500. Outer shaft 506 includes openings or windows 520A, 520B, 520C formed through a sidewall thereof at circumferentially spaced-apart positions that permit self-expansion of wings 518A, 518B, 518C when the windows are circumferentially aligned with the wings. As described above respect to outer shaft 206, in order to deploy wings 518A, 518B, 518C, outer shaft 506 is rotated or turned in order to circumferentially align windows 520A, 520B, 520C and wings 518A, 518B, 518C.

Figure 6:
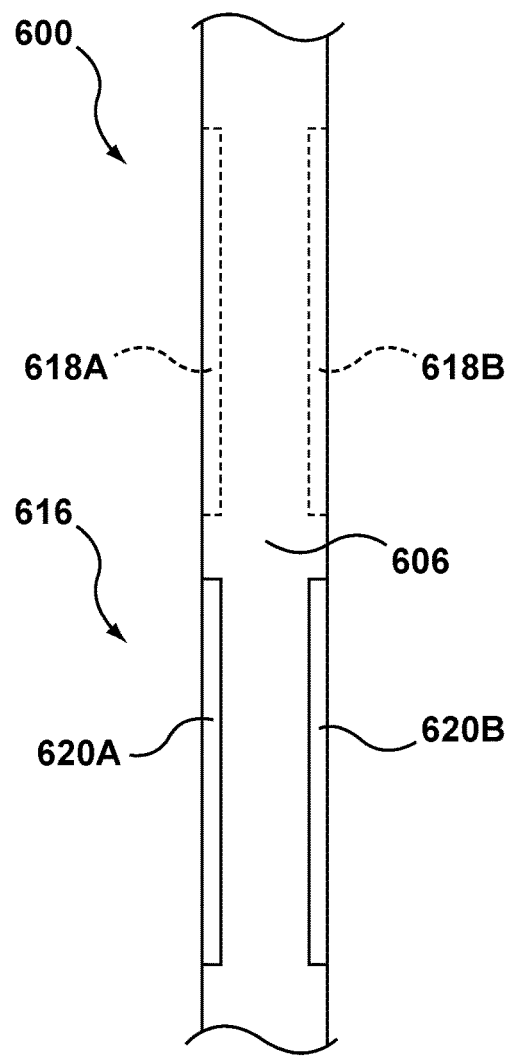
FIG. 6 is a side view of a portion of a delivery system having an integral centering mechanism according to another embodiment hereof, wherein translation deploys the centering mechanism and the centering mechanism is in a delivery or unexpanded configuration.
Figure 7:
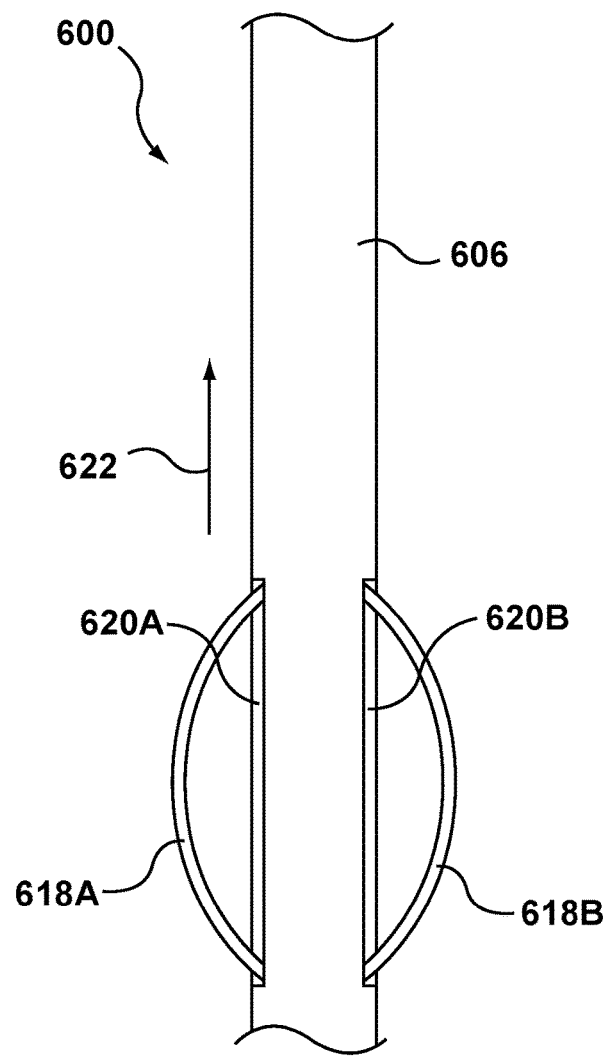
FIG. 7 is a side view of a portion of the delivery system of FIG. 6, wherein the centering mechanism is in a deployed or expanded configuration.

In another embodiment hereof, rather than deploying the centering mechanism via rotation of the outer shaft, the outer shaft may be translated in order to align the windows and the wings. More particularly, a portion of a delivery system 600 having a centering mechanism 616 is shown in FIG. 6 with wings 618A, 618B collapsed or compressed into a delivery configuration and in FIG. 7 with wings 618A, 618B in a deployed or expanded configuration. Outer shaft 606 includes openings or windows 620A, 620B formed through a sidewall thereof at circumferentially opposing positions. Openings or windows 620A, 620B are circumferentially aligned with wings 218A, 218B. However, when compressed or collapsed as shown in FIG. 6, openings or windows 620A, 620B are longitudinally offset or not aligned with wings 618A, 618B such that the wings are contained within outer shaft 606. When it is desired to deploy or expand centering mechanism 616, outer shaft 606 is proximally retracted as indicated by directional arrow 622 on FIG. 7 in order to longitudinally align windows 620A, 620B with wings 618A, 618B. Once the windows are aligned with the wings, wings 618A, 618B are exposed and permitted to self-expand similar to wings 218A, 218B described above.

In another embodiment hereof, the wings may be formed via elongated flat or ribbon-like elements. More particularly, with reference to FIG. 8, a flat or ribbon-like elongated element 828 is shown removed from a delivery system for sake of illustration only. Elongated element 828 is formed from a self-expanding material and shape-set in the deployed or expanded configuration shown in FIG. 8. Elongated element 828 has a proximal portion 830 and a distal portion 831 that includes two consecutive or sequential wings 818A. When disposed in a delivery system (not shown), at least two elongated elements would be housed between the outer and inner shafts of the delivery system at circumferentially opposing locations. A second or distal end 824A of each elongated element 828 is unattached or free to slide over the inner shaft of the delivery system, while a first or proximal end 826A is attached or anchored to the inner shaft. When it is desired to deploy or expand sequential wings 818A, the outer shaft (not shown) of the delivery system is longitudinally translated as described above with respect to the embodiment of FIGS. 6-7 or is rotated as described above with respect to the embodiment of FIGS. 4-5 in order to align sequential wings 818A with two sequential openings or windows (not shown) of the outer shaft of the delivery system. Once the windows are aligned with the wings, sequential wings 818A are exposed and permitted to self-expand similar to wings 218A, 218B and/or wings 618A, 618B described above. More particularly, unattached or free second end 824A of each elongated element 828 slides over the inner shaft in a proximal direction towards attached or anchored first end 826A. Sequential wings 818A resume their shape-set deployed or expanded configuration when permitted to radially expand through the aligned windows.

In another embodiment hereof, flat or ribbon-like elongated element 828 is not required to be formed from a self-expanding material and shape-set in the deployed or expanded configuration. Rather, a first or proximal end 826A of elongated element 828 is unattached or free to slide over the inner shaft (not shown) of the delivery system, while a second or distal end 824A is attached or anchored to the inner shaft. First or proximal end 826A is distally advanced by a user with a push rod (not shown) such that portions of element 828 are pushed or extended through two sequential openings or windows (not shown) of the outer shaft of the delivery system, thereby forming deployed sequential wings 818A. In this embodiment, the amount or degree of radial expansion may be controlled by the user. More particularly, the user may selectively increase the amount or degree of radial expansion, or height of wings 818A, by further distally advancing the push rod and thereby further pushing elongated element 828 to cause an additional amount or length of elongated element 828 to be pushed or extended through the two sequential openings or windows of the outer shaft. In another embodiment hereof (not shown), radial expansion or deployment of the wings may collectively operate similar to a Chinese finger cuff or finger trap. In a first state or configuration, the wings collectively have a relatively slim or narrow profile and in a second state or configuration, the wings collectively have a relatively thick or wide profile that contacts the vessel wall in order to wedge or center the delivery system within the vessel. When stability or centering is desired, opposing ends of each wing are pushed together in order to transform the wings into the second state or configuration in which the wings collectively have a relatively thick or wide profile that contacts the vessel wall.

In any embodiment hereof, the inner shaft may include grooves or tracks to assist in sliding and deployment of the wings. For example, FIGS. 9 and 9A illustrates an exemplary inner shaft 910 removed from a delivery system for illustration purposes only. Inner shaft 910 defines a lumen 912 for receiving a guidewire 914 there-through. Inner shaft 910 includes a longitudinal groove 932 formed on an outside surface thereof for receiving wings such as but not limited to wings 218A/218B, wings 618A/618B, and/or elongated element 828 having wings 818A formed thereon. Groove 932 serves as a track or pathway for the wing when it is sliding during deployment thereof.

Figure 10:
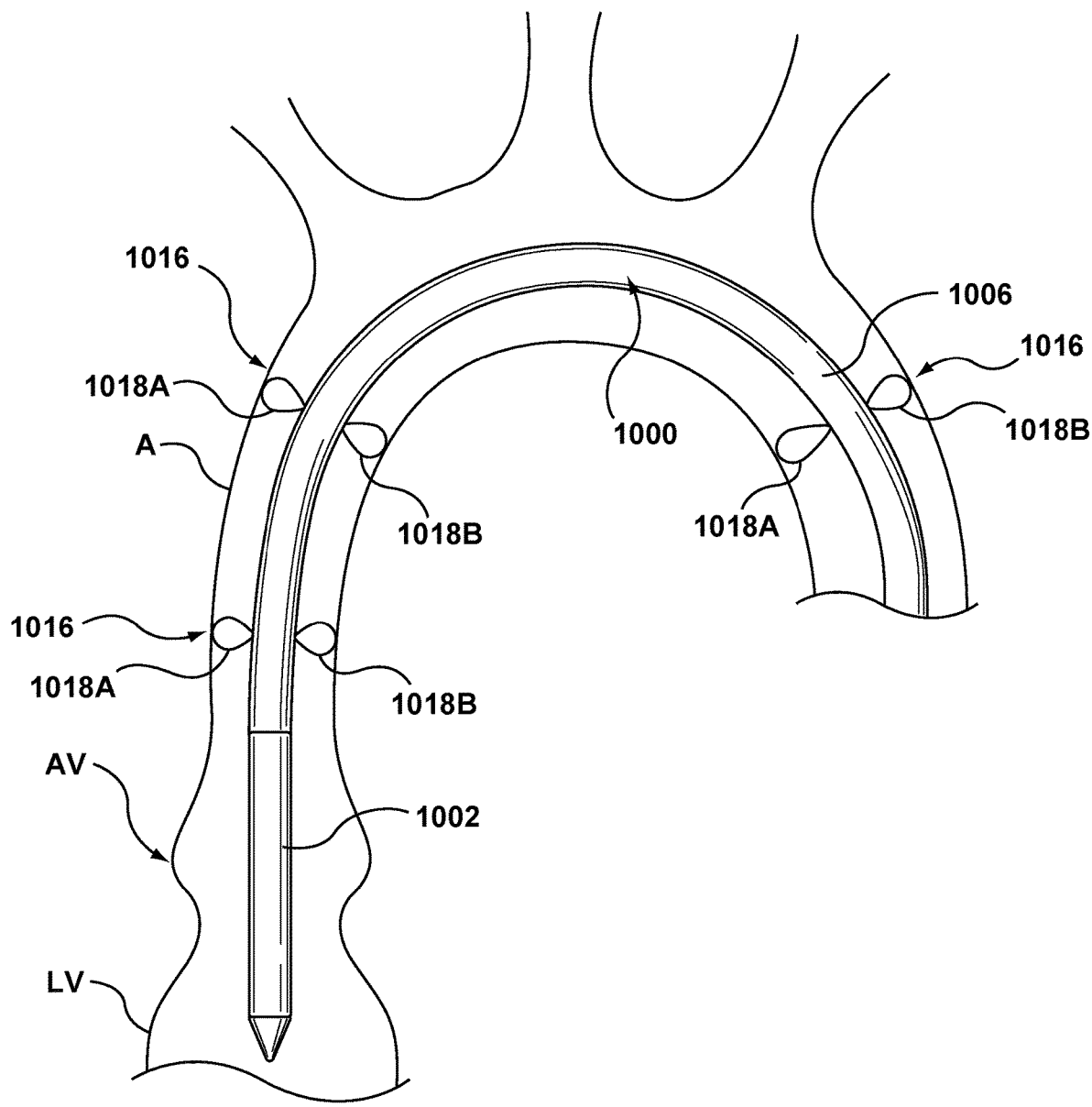
FIG. 10 is an illustration of a delivery system having an integral centering mechanism according to an embodiment hereof in situ, wherein the centering mechanism is in a deployed or expanded configuration.

FIG. 10 illustrates another embodiment hereof in which the wings of the centering mechanism have a different deployed configuration. In FIG. 10, a delivery system 1000 is depicted in situ, with centering mechanisms 1016 in a deployed or expanded configuration and a prosthetic heart valve (not shown) in a delivery or compressed configuration in which the prosthetic heart valve is loaded within a distal capsule section 1002 of the delivery system. In this embodiment, delivery system 1000 is shown with three centering mechanisms 1016 at longitudinally spaced-apart locations. A first centering mechanism 1016 is positioned proximal to distal capsule section 1002, a second centering mechanism 1016 is positioned to deploy within the aorta A distal to the branches of the aortic arch, and a third centering mechanism 1016 is positioned to deploy within the aorta A proximal to the branches of the aortic arch. Similar to centering mechanisms 216, each centering mechanism 1016 includes at least two expandable arms or wings 1018A, 1018B that, when expanded or deployed, are configured to deflect off of the vessel wall, i.e., aorta A, in order to push delivery system 1000 away from the walls of the vessel and center the delivery system within the vessel for a more successful prosthetic valve deployment. Each wing 1018A, 1018B is an individual or separate flat or ribbon-like element that is formed from a self-expanding material and shape-set in the deployed or expanded configuration shown in FIG. 10. In this embodiment the deployed configuration of wings 1018A, 1018B differs from the deployed configuration of wings 218A, 218B because wings 1018A, 1018B are each configured to extend circumferentially or transversely around the perimeter of outer shaft 1006 rather than extend longitudinally along the outer shaft. Although not shown in the view of FIG. 10, the openings or windows formed through outer shaft 1006 similar extend circumferentially around the perimeter of the outer shaft and outer shaft 1006 may be rotated (similar to outer shaft 206) or translated (similar to outer shaft 606) in order to align the windows with wings 1018A, 1018B.

Figure 11:
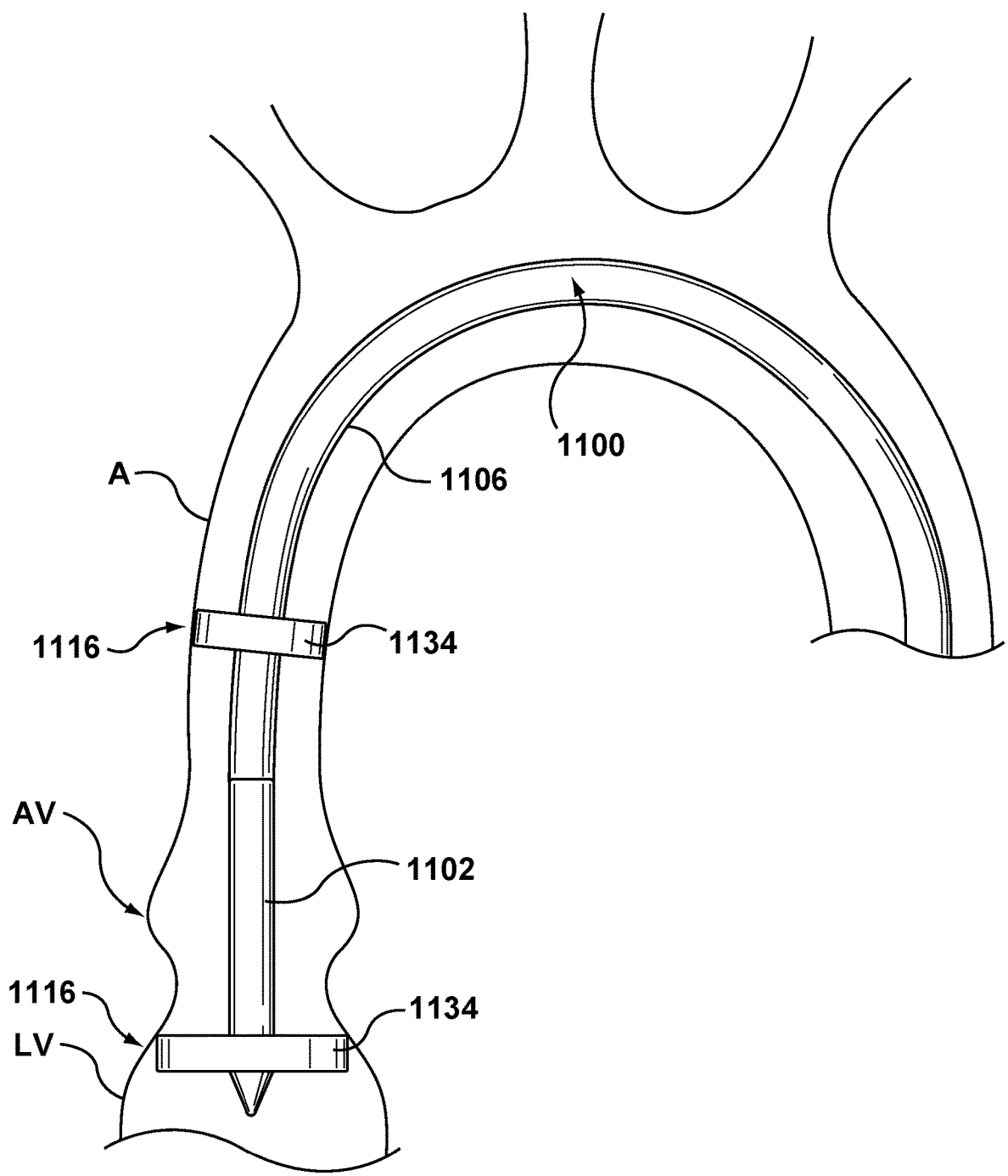
FIG. 11 is an illustration of a delivery system having an integral centering mechanism according to an embodiment hereof in situ, wherein the centering mechanism is a coiled wing and is shown in a deployed or expanded configuration.

FIG. 11 illustrates another embodiment hereof in which the centering mechanisms have a different deployed configuration. In FIG. 11, a delivery system 1100 is depicted in situ, with centering mechanisms 1116 in a deployed or expanded configuration and a prosthetic heart valve (not shown) in a delivery or compressed configuration in which the prosthetic heart valve is loaded within a distal capsule section 1102 of the delivery system. In this embodiment, delivery system 1100 is shown with two centering mechanisms 1116 at longitudinally spaced-apart locations with a first centering mechanism 1116 is positioned distal to distal capsule section 1102 and a second centering mechanism 1116 is positioned to deploy within the aorta A distal to the branches of the aortic arch. However, delivery system 1100 may be modified to include fewer centering mechanisms or additional centering mechanisms and the longitudinal position of the centering mechanisms may vary according to application. In this embodiment, each centering mechanism 1116 includes a coiled wing 1134 that, when expanded or deployed, is configured to deflect off of the vessel wall, i.e., aorta A, in order to push delivery system 1100 away from the walls of the vessel and center the delivery system within the vessel for a more successful prosthetic valve deployment. Each coiled wing 1134 is an individual or separate flat or ribbon-like element that is formed from a self-expanding material and shape-set in the deployed or expanded configuration shown best in FIG. 14. The flat or ribbon-like element that forms coiled wing 1134 distributes deployment forces onto the vessel wall.

Figure 12:
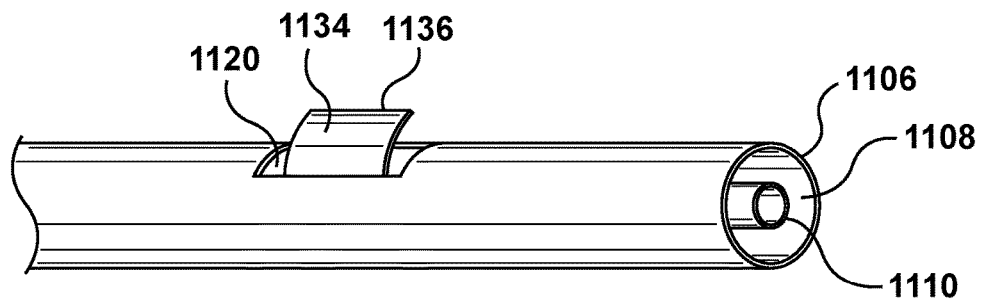
FIG. 12 is a perspective view of a portion of the delivery system of FIG. 11, wherein the centering mechanism is primarily in a delivery or unexpanded configuration with only a first end thereof being deployed.

During delivery of delivery system 1100, each coiled wing 1134 is compressed into a delivery configuration in which the coiled wing is enclosed or housed between an outer shaft 1106 and an inner shaft 1110 of the delivery system, within lumen 1108 of outer shaft 1106 shown in FIG. 12. Inner shaft 1110 is rotatable relative to outer shaft 1106. More particularly, FIG. 12 illustrates a portion of delivery system 1100 wherein only a second or free end 1136 of the coiled wing extends through an opening or window 1120 formed in outer shaft 1106 and the remaining length of the coiled wing is wrapped around inner shaft 1110 and housed within lumen 1108 of the delivery system. In addition, FIG. 13 illustrates coiled wing 1134 in its compressed or delivery configuration and removed from the delivery system for sake of illustration only. When each centering mechanism 1116 in its compressed or delivery configuration, each coiled wing 1134 winds in a series of one or more loops around an outer surface of inner shaft 1110 in a helical or corkscrew fashion and consecutive or adjacent loops thereof are stacked against and contacting each other with substantially no space therebetween. Stated another way, when the centering mechanisms are in a delivery configuration, each wing 1134 has a series of windings that extend around inner shaft 1110 such that each winding is enclosed between the outer and inner shafts. Each coiled wing 1134 has a first end 1138 that is attached or anchored to inner shaft 1110 and second or opposing end 1136 that is unattached so that the second end is free to extend through window 1120 for deployment and recapture as will be explained in more detail herein. First end 1138 of coiled wing 1134 is attached to inner shaft 1110 via bonding or adhesive. Window 1120 is formed through a sidewall of outer shaft 1106 and is circumferentially and longitudinally aligned with second or free end 1136 of coiled wing 1134.

When it is desired to deploy or expand centering mechanisms 1116, inner shaft 1110 is rotated or turned relative to outer shaft 1106 as indicated by directional arrow 1122 on FIG. 14. More particularly, as inner shaft 1110 is rotated, second or free end 1136 of coiled wing 1134 extends through window 1120 and coiled wing 1134 begins to wrap or wind around the perimeter of outer shaft 1106. In an embodiment, second or free end 1136 of coiled wing 1134 is slightly rounded at the edges thereof in order to be atraumatic and extends through window 1120 at approximately a 45 degree angle relative to window 1120. Inner shaft 1110 is rotated until the entire length of coiled wing 1134 extends through window 1120 as shown in FIG. 14, and coiled wing 1134 is permitted to self-expand to its shape-set deployed or expanded configuration. FIG. 15 illustrates coiled wing 1134 in its deployed or expanded configuration and removed from the delivery system for sake of illustration only. When each centering mechanism 1116 is in its deployed or expanded configuration, each coiled wing 1134 winds in a series of one or more loops or windings around an outer surface of outer shaft 1106 in a helical or corkscrew fashion and consecutive or adjacent loops thereof are spaced apart from each other and not contacting each other. Stated another way, coiled wing 1134 is deployed around and encircles outer shaft 1106 and consecutive or adjacent loops thereof have incrementally decreasing diameters such that gaps or spaces extend between the adjacent loops in order to allow blood to flow therebetween.

As shown in FIG. 14, the windings of coiled wing 1134 extend in a single plane that is transverse to delivery system 1100. In order to retract or recapture coiled wing 1134, inner shaft 1110 is rotated in the opposite direction from directional arrow 1122. Coiled wing 1134 is pulled back into lumen 1108 of outer shaft 1106 and winds or wraps around inner shaft 1110 in the delivery configuration described above with respect to FIGS. 12 and 13.

Figure 12A:
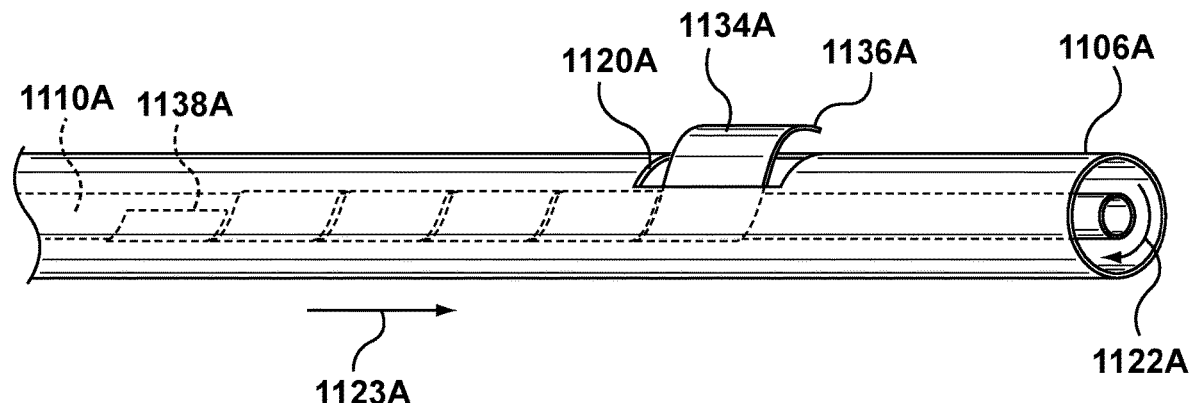
FIG. 12A is a perspective view of a portion of the delivery system having an integral centering mechanism according to an embodiment hereof in situ, wherein the centering mechanism is a coiled wing with windings that longitudinally extend to form a conical profile and the centering mechanism is primarily in a delivery or unexpanded configuration with only a first end thereof being deployed.

In another embodiment shown in FIG. 12A and FIG. 14A, the windings of a coiled wing 1134A longitudinally extend to form a conical profile. FIG. 12A illustrates a portion of a delivery system wherein only a second or free end 1136A of the coiled wing extends through an opening or window 1120A formed in outer shaft 1106A and the remaining length of the coiled wing is wrapped around inner shaft 1110A. Deployment of coiled wing 1134A is similar to deployment of coiled wing 1134 except that inner shaft 1110A moves distally as indicated by directional arrow 1123A as it is being rotated in order to allow coiled wing 1134A to deploy out of window 1120A. More particularly, when it is desired to deploy or expand coiled wing 1134A, inner shaft 1110A is rotated or turned relative to outer shaft 1106A as indicated by directional arrow 1122A on FIG. 12A. As inner shaft 1110A is rotated and moves distally, second or free end 1136A of coiled wing 1134A extends through window 1120A and coiled wing 1134A forms a conical coil around the perimeter of outer shaft 1106A as second or free end 1136A progresses or moves distally relative to outer shaft 1106A. Inner shaft 1110A is rotated until the entire length of coiled wing 1134A extends through window 1120A as shown in FIG. 14A, and coiled wing 1134A is permitted to self-expand to its shape-set deployed or expanded configuration.

Figures 16, 16A:
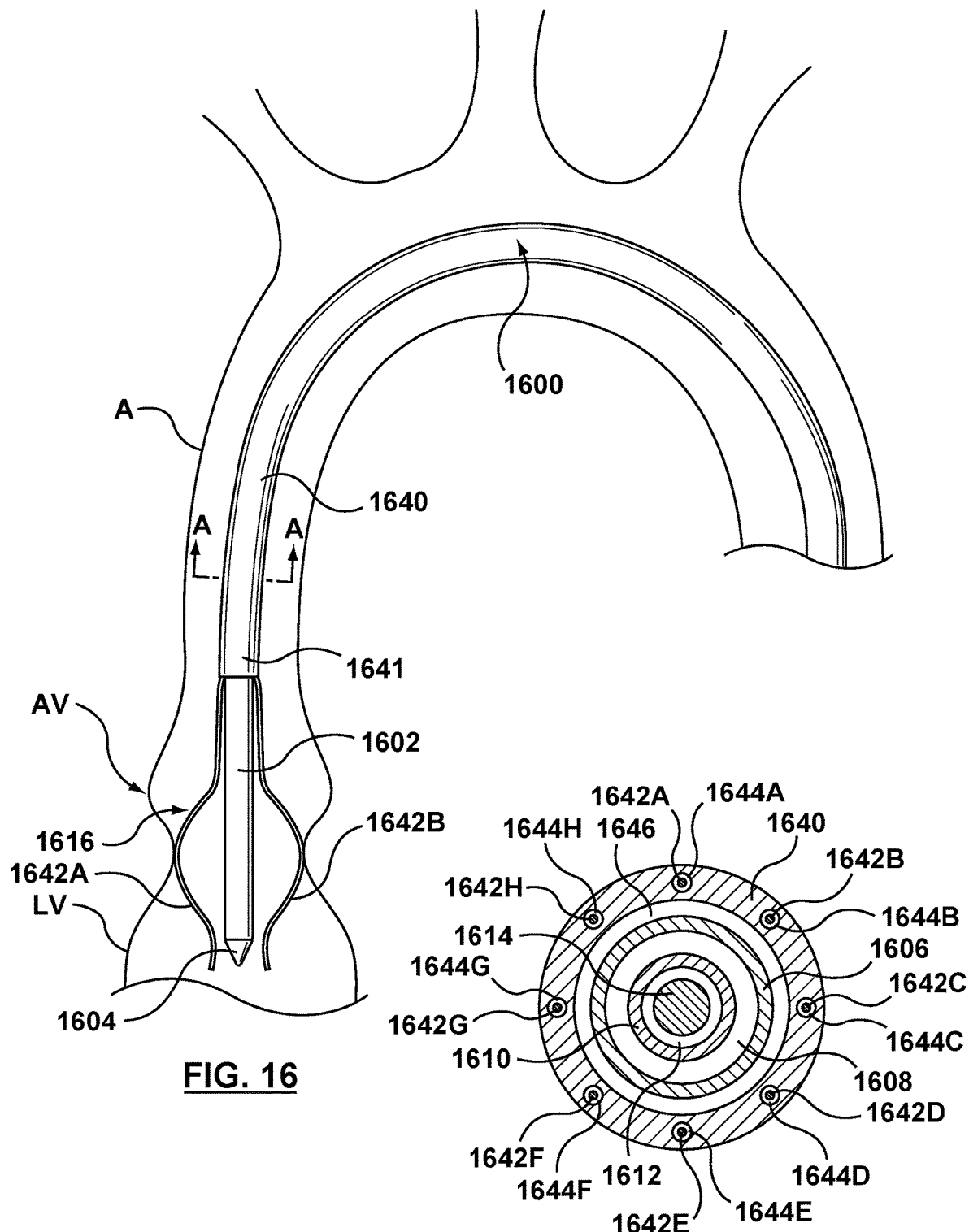
FIG. 16 is an illustration of a delivery system having an integral centering mechanism according to an embodiment hereof in situ, wherein the centering mechanism includes a plurality of extendible self-expanding filaments and is shown in a deployed or expanded configuration.
FIG. 16A is a cross-sectional view taken along line A-A of FIG. 16.

FIGS. 16 and 16A illustrates another embodiment hereof in which the centering mechanism includes self-expanding multiple filaments that may be selectively deployed at or adjacent to the native valve annulus. In FIG. 16, a delivery system 1600 is depicted in situ, with centering mechanism 1616 in a deployed or expanded configuration and a prosthetic heart valve (not shown) in a delivery or compressed configuration in which the prosthetic heart valve is loaded within a distal capsule section 1602 of the delivery system. In this embodiment, centering mechanism 1616 includes a plurality of self-expanding elongated filaments 1642A, 1642B, 1642C, 1642D, 1642E, 1642F, 1642G, 1642H (collectively referred to herein as elongated filaments 1642) that, when expanded or deployed, are configured to deflect off of the native valve anatomy in order center distal capsule portion 1602 of the delivery system within the native valve annulus for a more successful prosthetic valve deployment. Although centering mechanism 1616 is shown with eight filaments circumferentially spaced apart, centering mechanism 1616 may include a greater number of filaments or a fewer number of filaments, depending upon application. Each elongated filament 1642 is an individual or separate strand having at least a distal portion thereof formed from a self-expanding material and shape-set in the deployed or expanded configuration shown in FIG. 16.

In this embodiment, in addition to an outer shaft 1606 that defines a lumen 1608 and an inner shaft 1110 that defines a central lumen 1612 for receiving a guidewire 1614, delivery system 1600 includes an additional outermost shaft 1640. Outer shaft 1606 is positioned within a lumen 1646 defined by outermost shaft 1640. Outermost shaft 1640 is shorter than outer shaft 1606, with a distal end 1641 positioned proximal to a proximal end of distal capsule portion 1602. In an embodiment hereof, distal end 1641 is positioned between 6-8 cm from a distal end 1604 of delivery system 1600. Outermost shaft 1640 includes a plurality of lumens 1644A, 1644B, 1644C, 1644D, 1644E, 1644F, 1644G, 1644H (collectively referred to herein as lumens 1644) formed in a sidewall thereof for housing or receiving elongated filaments 1642A, 1642B, 1642C, 1642D, 1642E, 1642F, 1642G, 1642H, respectively. Although outermost shaft 1640 is shown with eight lumens circumferentially spaced apart, it will be understood by one of ordinary skill in the art that the number of lumens corresponds to the number of filaments utilized therein, which may vary according to application as described above. Elongated filaments 1642 are slidingly positioned within lumens 1644, and elongated filaments 1642 may be moved relative to outermost shaft 1640 in order to selectively deploy or expand elongated filaments 1642.

During delivery of delivery system 1600, each elongated filament 1642 is compressed into a delivery configuration in which the entire length of each filament is housed within its respective lumen 1644 of outermost shaft 1640. When in its compressed or delivery configuration, the distal portion of each elongated filament 1642 has a straightened profile that is enclosed within one of lumens 1644 formed in the sidewall of outermost shaft 1640. When it is desired to deploy or expand centering mechanism 1616, elongated filaments 1642 are distally advanced by the user such that the distal portions thereof are exposed or extend out of outermost shaft 1640 and the distal portion of each elongated filament 1642 is permitted to self-expand to their shape-set deployed or expanded configuration in which the distal portion of each elongated filament has a curved, bowed profile. Elongated filaments 1642 may be simultaneously deployed at the same time, or may be individually deployed as needed. Outermost shaft 1640 and elongated filaments 1642 housed therein do not move when distal capsule portion 1602 is retracted in order to deploy the prosthetic heart valve, thus ensuring that delivery system 1600 remains circumferentially centered within the native anatomy during deployment of the prosthetic heart valve. After the prosthetic heart valve is deployed as desired, in order to retract or recapture centering mechanism 1616, elongated filaments 1642 are proximally retracted by the user such that the distal portions thereof are pulled back into their respective lumen 1644 of outermost shaft 1640.

Figure 17:
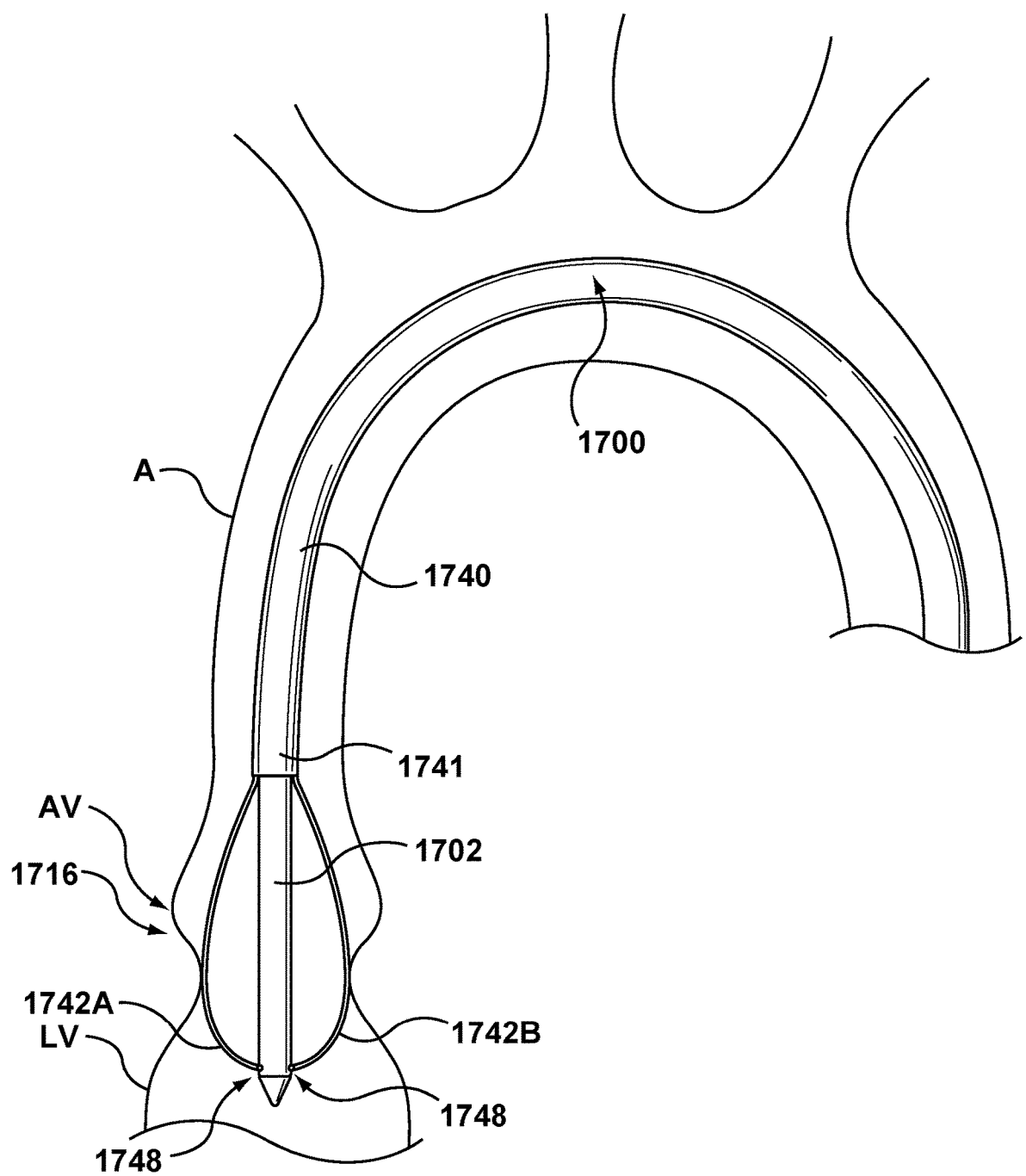
FIG. 17 is an illustration of a delivery system having an integral centering mechanism according to an embodiment hereof in situ, wherein the centering mechanism includes a plurality of filaments that may be selectively bowed or expanded and is shown in a deployed or expanded configuration.

FIG. 17 illustrates another embodiment hereof in which, similar to the embodiment of FIG. 16, the centering mechanism includes multiple filaments that may be selectively deployed at or adjacent to the native valve annulus. However, in the embodiment of FIG. 17, rather than being shape-set or formed from a self-expanding material, the distal ends of the filaments are fixed so that distal advancement of the filaments results in the distal portions thereof bulging radially outward as shown in FIG. 17. More particularly, in FIG. 17, a delivery system 1700 is depicted in situ, with centering mechanism 1716 in a deployed or expanded configuration and a prosthetic heart valve (not shown) in a delivery or compressed configuration in which the prosthetic heart valve is loaded within a distal capsule section 1702 of the delivery system. Similar to centering mechanism 1616, centering mechanism 1716 includes a plurality of elongated filaments although only elongated filaments 1742A, 1742B are visible in the side view of FIG. 17. Each elongated filament 1742 is an individual or separate strand that, when the distal portion thereof is expanded or deployed, are configured to deflect off of the native valve anatomy in order center distal capsule portion 1702 of the delivery system within the native valve annulus for a more successful prosthetic valve deployment. Distal end 1748 of each elongated filament 1742 is attached or fixed to an outer surface of distal capsule portion 1702. Delivery system 1700 includes an additional outermost shaft 1740 which is similar to outermost shaft 1640 described above and includes a plurality of lumens (not shown in FIG. 17) formed in a sidewall thereof for receiving elongated filaments 1742. Elongated filaments 1742 are slidingly positioned within the lumens of outermost shaft 1740, and elongated filaments 1742 may be moved relative to outermost shaft 1740 in order to selectively deploy or expand elongated filaments 1742 as will be described in more detail herein. A distal end 1741 is positioned proximal to a proximal end of distal capsule portion 1702.

During delivery of delivery system 1700, each elongated filament 1742 is housed within its respective lumen of outermost shaft 1740 with a distal portion of each elongated filament 1742 extending over an outer surface of distal capsule portion 1702. During delivery, distal portions of elongated filaments 1742 have a straightened profile that is flush against the outer surface of distal capsule portion 1702. When it is desired to deploy or expand centering mechanism 1716, the proximal ends of elongated filaments 1742 are distally advanced by the user such that the distal portions thereof bow or bulge radially outwards as shown in FIG. 17. When each elongated filament 1742 is in an expanded configuration, the distal portion thereof has a curved, bowed profile radially spaced apart from the outer surface of distal capsule portion 1702. With distal ends 1748 thereof attached to distal capsule portion 1702, elongated filaments 1742 move proximally with distal capsule portion 1702 when the distal capsule portion is retracted in order to deploy the prosthetic heart valve. After the prosthetic heart valve is deployed as desired, in order to retract or recapture centering mechanism 1716, the proximal ends of elongated filaments 1742 are proximally retracted by the user such that the bulged or bowed distal portions thereof are straightened back into their delivery configuration in which the distal portions of elongated filaments 1742 are flush with the outer surface of distal capsule portion 1702.

The longitudinal position of centering mechanism 1716 may vary according to application. For example, in another embodiment hereof (not shown), the distal end 1748 of each elongated filament 1742 may be attached or fixed to an outer surface of the outer shaft (not shown) rather than to distal capsule portion 1702. The distal portions of the filaments are thus positioned to be deployed within ascending aorta and/or aortic arch in order center distal capsule portion 1702 of the delivery system within the native valve annulus for a more successful prosthetic valve deployment. In this embodiment, the outer shaft and deployed distal ends of each elongated filament do not move when distal capsule portion 1702 is retracted in order to deploy the prosthetic heart valve, thus ensuring that delivery system 1700 remains circumferentially centered within the native anatomy during deployment of the prosthetic heart valve.

Figure 18:
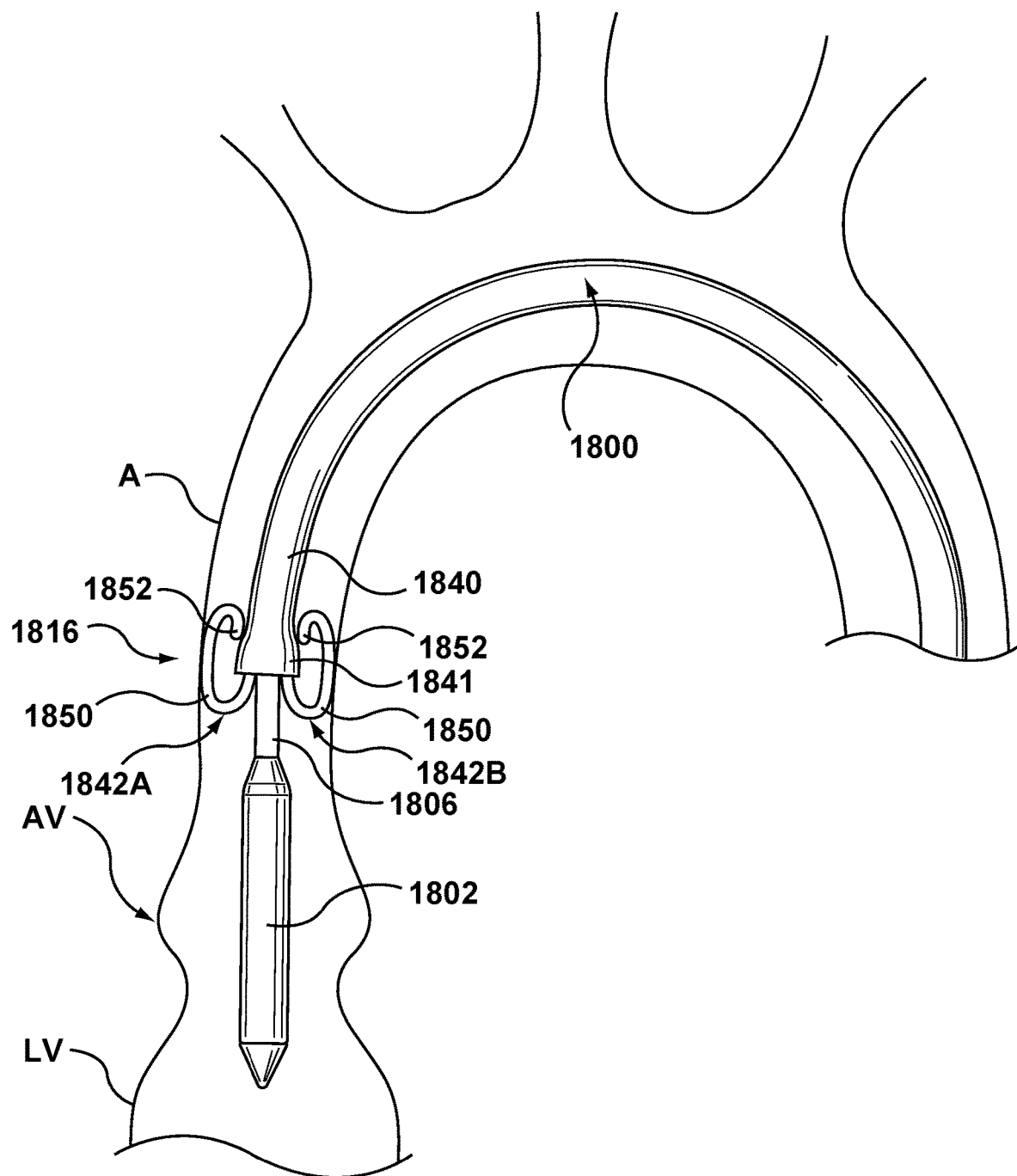
FIG. 18 is an illustration of a delivery system having an integral centering mechanism according to an embodiment hereof in situ, wherein the centering mechanism includes a plurality of extendible self-expanding filaments with a soft, curled distal end and is shown in a deployed or expanded configuration.
Figure 19:
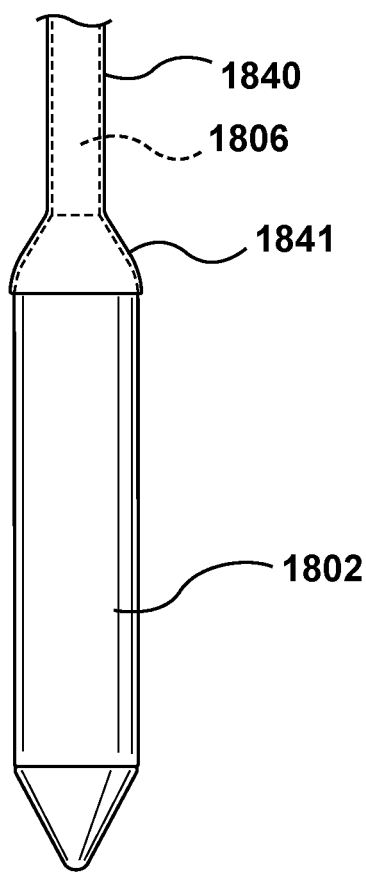
FIG. 19 is a side view of a portion of the delivery system of FIG. 18.

FIGS. 18 and 19 illustrate another embodiment hereof in which, similar to the embodiment of FIG. 16, the centering mechanism includes multiple self-expanding filaments that may be selectively deployed. However, in the embodiment of FIG. 18, rather than being deployed at or adjacent to the native valve annulus, the filaments include soft or flexible ends that are deployed within the aorta A distal to the branches of the aortic arch to deflect off of the vessel wall, i.e., aorta A, in order to push delivery system 1800 away from the walls of the vessel and center the delivery system within the vessel for a more successful prosthetic valve deployment. More particularly, in FIG. 18, a delivery system 1800 is depicted in situ, with centering mechanism 1816 in a deployed or expanded configuration and a prosthetic heart valve (not shown) in a delivery or compressed configuration in which the prosthetic heart valve is loaded within a distal capsule section 1802 of the delivery system. Delivery system 1800 includes an additional outermost shaft 1840 which is similar to outermost shaft 1840 described above and includes a plurality of lumens (not shown in FIG. 18) for receiving a plurality of filaments 1842. Outermost shaft 1840 extends over an outer shaft 1806. Filaments 1842 are slidingly positioned within the lumens of outermost shaft 1840, and filaments 1842 may be moved relative to outermost shaft 1840 in order to selectively deploy or expand filaments 1842 as will be described in more detail herein. A distal end 1841 of outermost shaft 1840 is positioned proximal to a proximal end of distal capsule portion 1802.

Similar to centering mechanism 1616, centering mechanism 1816 includes a plurality of self-expanding filaments although only filaments 1842A, 1842B are visible in the side view of FIG. 18. Each filament 1842 is an individual or separate elongated strand having a relatively softer and more flexible distal portion 1850 relative to the length proximal thereto. For example, suitable materials for distal portion 1850 include flexible polymeric materials such as polyethylene or polypropylene, while the remaining length of filament 1842 may be formed from or reinforced with Nitinol or stainless steel for increased strength and pushability. Distal portion 1850 of each filament 1842 is self-expanding and pre-formed such that the distal portion curls radially outward and longitudinally in a proximal direction when extended from distal end 1841 of outermost shaft 1840. More particularly, as shown in FIG. 18, when deployed distal portion 1850 of each filament 1842 radially expands to contact the vessel wall and a distal end 1852 of each filament 1842 curls underneath itself to contact an outer surface of outermost sheath 1840. Distal end 1852 may be covered with soft material such as silicone or rubber to prevent atraumatic damage to the vessel wall as it is advancing. The curled deployed configurations of distal portions 1850 of filaments 1842 apply a spring force against the vessel wall and provide stability by expanding between the vessel wall and the outer surface of outermost sheath 1840.

During delivery of delivery system 1800, each filament 1842 is compressed into a delivery configuration in which the entire length of each filament is housed within its respective lumen of outermost shaft 1840. When in its compressed or delivery configuration, each filament 1842 is straightened. As best shown in FIG. 19, during delivery of catheter 1800, distal end 1841 of outermost shaft 1850 abuts against a proximal end of distal capsule portion 1802. In an embodiment hereof, distal end 1841 may be funnel-shaped or flared in order to mate with the proximal end of distal capsule portion 1802. Such a flared configuration ensures that distal end 1841 is flush against the proximal end of distal capsule portion 1802 such that there is no leading edge during delivery. In addition, the flared configuration of distal end 1841 of outermost shaft 1840 aids in deployment of filaments 1842 because the funnel-shape or flare directs or guides distal ends 1852 of the filaments radially outward during deployment thereof.

When it is desired to deploy or expand centering mechanism 1816, outermost shaft 1840 is proximally retracted such that distal end 1841 thereof is spaced apart from distal capsule portion 1802 as shown in FIG. 18. By distancing outermost shaft 1840 from distal capsule 1802, filaments 1842 have sufficient space to be extended from outermost shaft 1840 and distal capsule portion 1802 has sufficient space to be proximally retracted during deployment of the prosthetic heart valve. Filaments 1842 are then distally advanced by the user such that distal portions 1850 thereof are exposed or extend out of outermost shaft 1840 and distal portions 1850 of filaments 1842 are permitted to self-expand to their shape-set deployed or expanded configuration shown in FIG. 18. Filaments 1842 may be simultaneously deployed at the same time, or may be individually deployed as needed in order to correct alignment of delivery system 1800. Outermost shaft 1840 and filaments 1842 housed therein do not move when distal capsule portion 1802 is retracted in order to deploy the prosthetic heart valve, thus ensuring that delivery system 1800 remains circumferentially centered within the native anatomy during deployment of the prosthetic heart valve. After the prosthetic heart valve is deployed as desired, in order to retract or recapture centering mechanism 1816, filaments 1842 are proximally retracted by the user such that the distal portions thereof are pulled back into their respective lumen of outermost shaft 1840.

Figure 20:
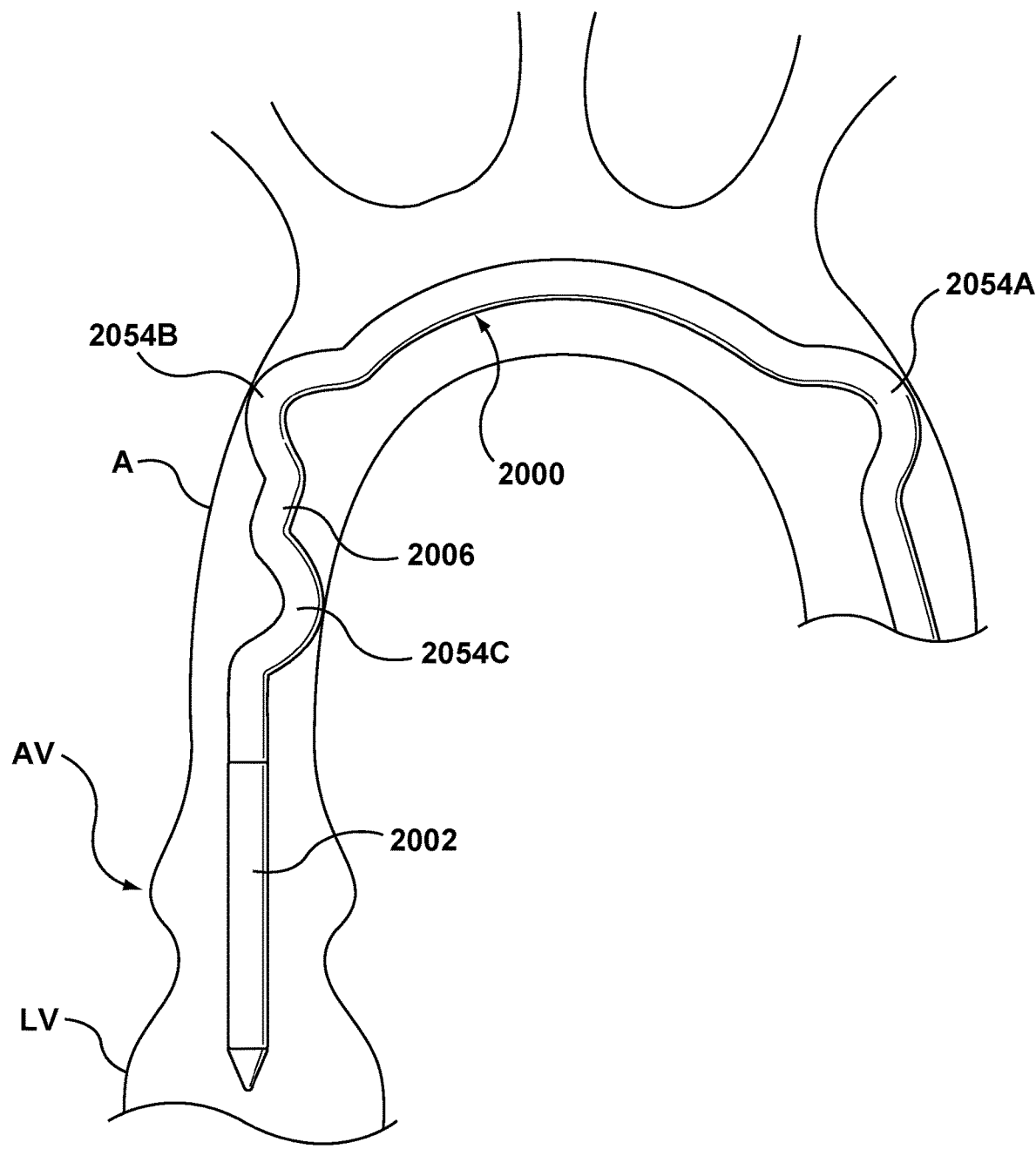
FIG. 20 is an illustration of a delivery system in which an outer shaft thereof is pre-formed or pre-shaped to include a plurality of deflection segments according to another embodiment hereof in situ, wherein the deflection segments are shown in a deployed or expanded configuration.
Figure 20A:
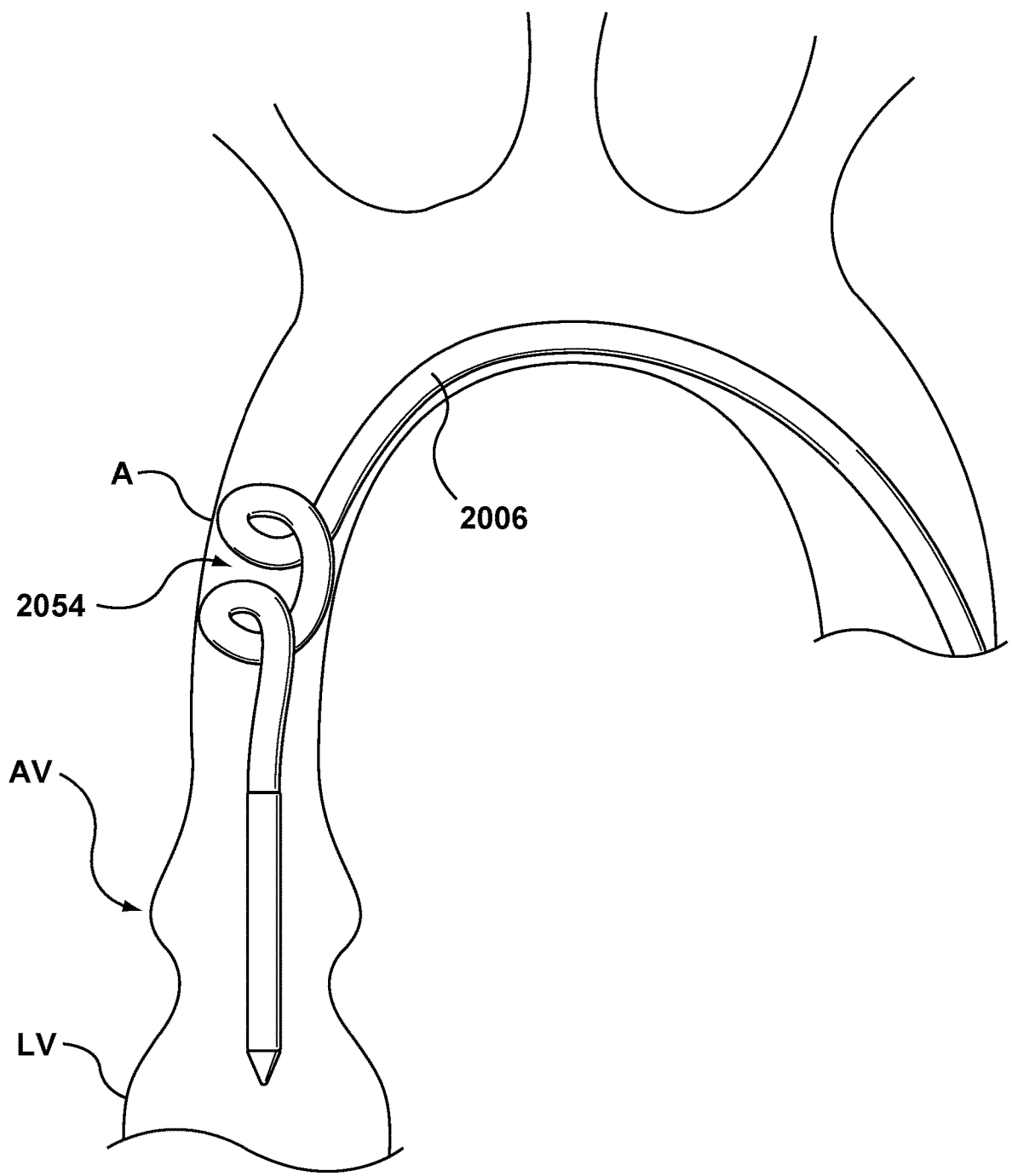
FIG. 20A is an illustration of a delivery system in which an outer shaft thereof is pre-formed or pre-shaped to include a plurality of deflection segments according to another embodiment hereof in situ, wherein the deflection segments are shown in a deployed or expanded configuration and the deflection segments form a portion of a spiral or corkscrew.

FIG. 20 illustrates another embodiment hereof in which the outer shaft of the delivery system may be pre-formed or pre-shaped to include a plurality of deflection segments 2054A, 2054B, 2054C. In FIG. 20, a delivery system 2000 is depicted in situ, with deflection segments 2054A, 2054B, 2054C in a deployed or expanded configuration and a prosthetic heart valve (not shown) in a delivery or compressed configuration in which the prosthetic heart valve is loaded within a distal capsule section 2002 of the delivery system. In this embodiment, outer shaft 2006 includes a plurality of deflection segments 2054A, 2054B, 2054C that are pre-shaped or pre-formed to deflect off of the native valve anatomy in order center distal capsule portion 2002 of the delivery system within the native valve annulus for a more successful prosthetic valve deployment. In this embodiment, delivery system 2000 is shown with three deflection segments at longitudinally spaced-apart locations. A first deflection segment 2054C is positioned proximal to distal capsule section 2002, a second deflection segment 2054B is positioned to deploy within the aorta A distal to the branches of the aortic arch, and a third deflection segment 2054A is positioned to deploy within the aorta A proximal to the branches of the aortic arch. However, delivery system 2000 may include only one or two deflection segments along a length thereof or may include more than three deflection segments at longitudinally spaced-apart locations along delivery system 2000. Each deflection segment 2054A, 2054B, 2054C is curved or arched such that it bows or bulges radially outward with respect to the remaining length of outer shaft 2006. Stated another way, each deflection segment 2054A, 2054B, 2054C has a curved, bowed profile with respect to the remaining length of outer shaft 2006. In the embodiment of FIG. 20, the deflection segments extend in the same plane, i.e., are co-planar, with respect to the remaining length of outer shaft 2006. In another embodiment hereof shown in FIG. 20A, one or more deflection segments 2054 extend in a different plane with respect to the remaining length of outer shaft 2006 such that deflection segments 2054 form a portion of a spiral or corkscrew.

During delivery of delivery system 2000, outer shaft 2006 is sufficiently flexible to deform into a substantially straight configuration in order to be percutaneously introduced into the vasculature. Once within the aorta, deflection segments 2054A, 2054B, 2054C of outer shaft 2006 are permitted to self-expand to their shape-set deployed or expanded configuration shown in FIG. 20. Since the abdominal aorta has a larger diameter than the aortic arch, deflection segments 2054A, 2054B, 2054C of outer shaft 2006 may be tracked through the abdominal aorta and into the aortic arch, whereby they contact the target vessel wall, i.e., aorta A, and deflect off of the vessel wall, i.e., aorta A, in order to push delivery system 2000 away from the walls of the vessel and center the delivery system within the vessel for a more successful prosthetic valve deployment.

Figure 21:
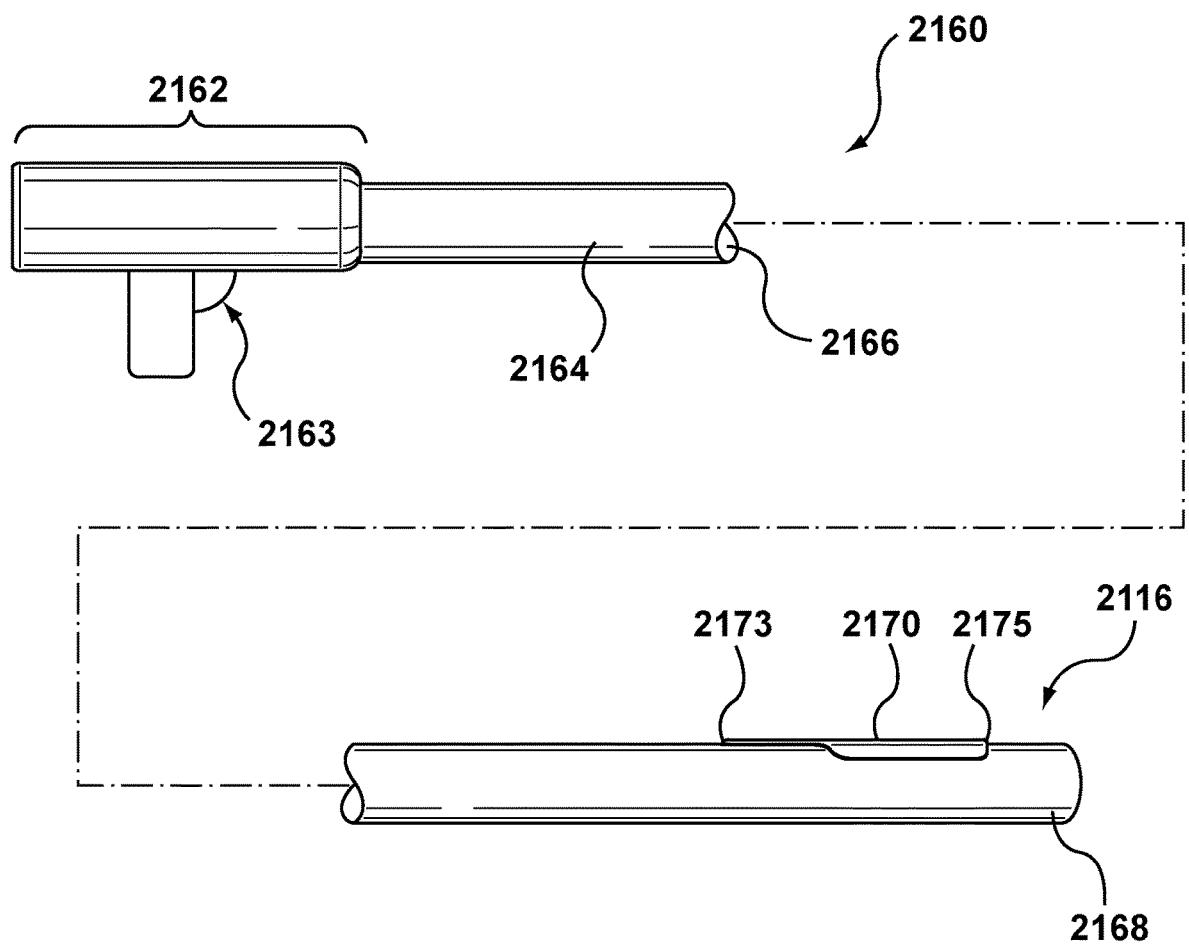
FIG. 21 is a side view illustration of a delivery system having a deployable lever arm according to an embodiment hereof, wherein the lever arm is shown in a delivery or unexpanded configuration.
Figure 22:
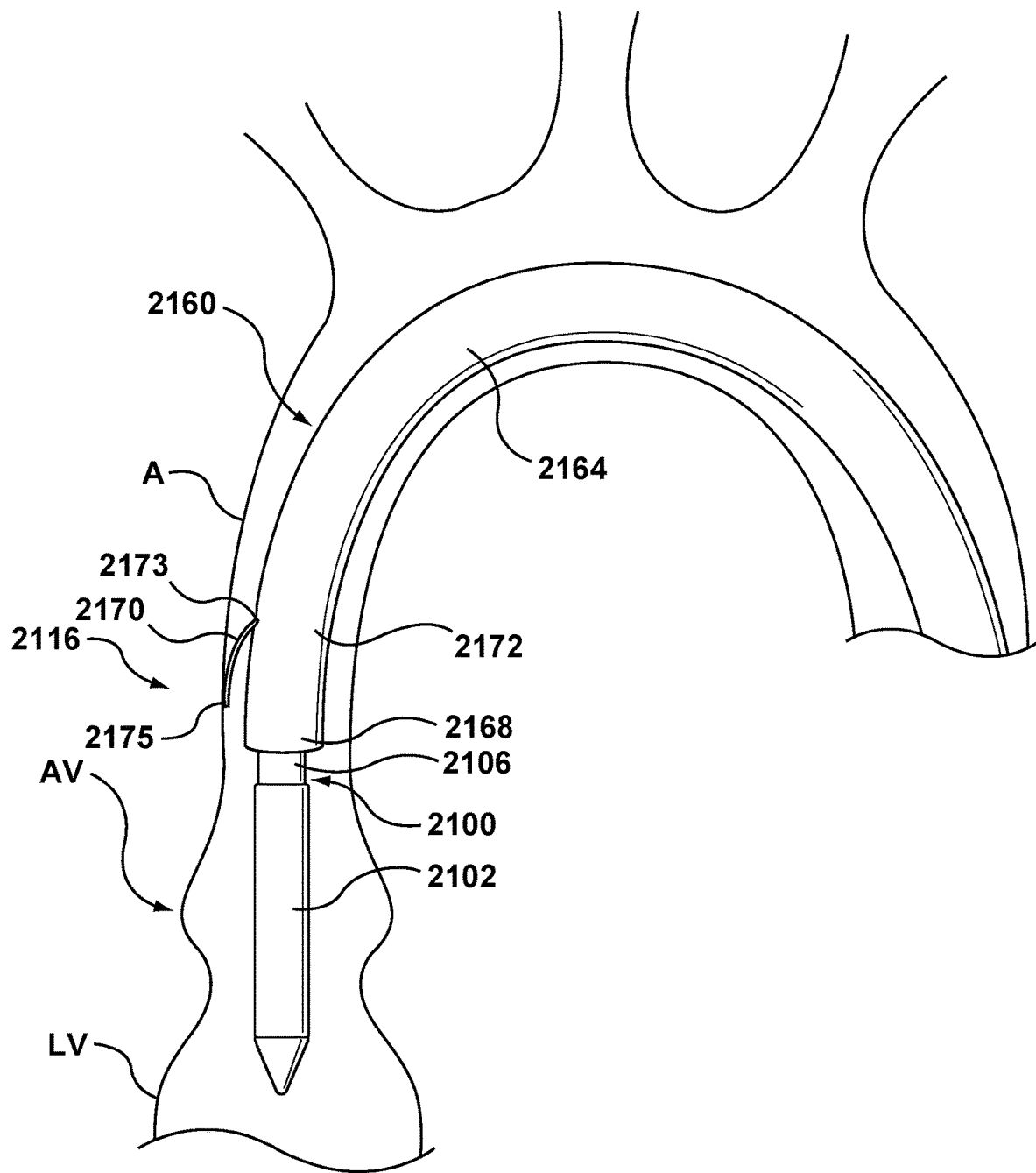
FIG. 22 is an illustration of the delivery system of FIG. 21 in situ, wherein the lever arm is shown in a deployed or expanded configuration.

FIGS. 21 and 22 illustrate another embodiment hereof in which a centering mechanism 2116 includes a lever arm that may be selectively deployed within the aorta A to deflect off of the vessel wall, i.e., aorta A, in order to push the delivery system away from the walls of the vessel and center the delivery system within the vessel for a more successful prosthetic valve deployment. The lever arm is coupled to a distal portion of a kicker tool that may be utilized separately or independently from the delivery system, or in another embodiment hereof (not shown), the kicker tool may be built into or onto the delivery system such that the kicker tool and delivery system are an integrated system. More particularly, FIG. 21 illustrates a side view of a kicker tool 2160 having a deployable lever arm 2170 while FIG. 22 illustrates kicker tool 2160 being utilized with a delivery system 2100. In FIG. 22, kicker tool 2160 and delivery system 2100 are depicted in situ, with lever arm 2170 in a deployed or expanded configuration and a prosthetic heart valve (not shown) in a delivery or compressed configuration in which the prosthetic heart valve is loaded within a distal capsule section 2102 of the delivery system. As shown in FIG. 22, kicker tool 2160 is distally advanced over outer shaft 2106 of delivery system 2100 until a distal end 2168 of the kicker tool is located proximal to a proximal end of distal capsule section 2102 of the delivery system.

Figure 21A:
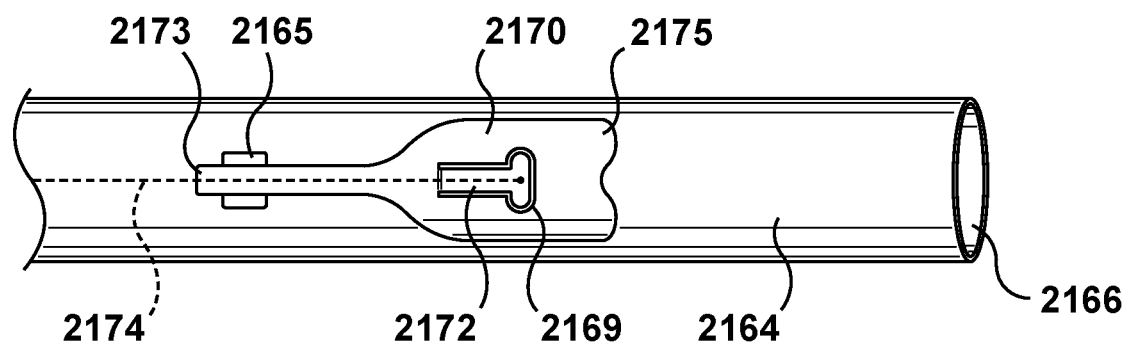
FIG. 21A is a top view illustration of a distal portion of the delivery system of FIG. 21, wherein the lever arm is shown in a delivery or unexpanded configuration.

Turning to FIG. 21 and FIG. 21A, kicker tool 2160 in its delivery configuration will be described in more detail. Kicker tool 2160 includes a shaft or tubular component 2164 that defines a lumen 2166 there-through. Shaft component 2164 includes a window 2165 formed through a sidewall thereof such that window 2165 is in fluid communication with lumen 2166. Window 2165 is positioned just proximal to lever arm 2170. A handle 2162 having a trigger 2163 is coupled to a proximal end of shaft component 2164, and lever arm 2170 is coupled to an exterior or outer surface of a distal portion of shaft component 2164. In this embodiment, lever arm 2170 is an individual or separate flat or ribbon-like element having a first or proximal end 2173 and a second or distal end 2175. In another embodiment hereof (not shown), the kicker tool may include a plurality of lever arms configured to deflect off of the vessel wall. First or proximal end 2173 is fixed or attached to the exterior or outer surface of shaft component 2164, while second or distal end 2175 is free or unattached to shaft component 2164. Second or distal end 2175 of lever arm 2170 is slightly rounded at the edges thereof in order to be atraumatic when deployed against the vessel wall. Lever arm 2170 includes a cut-out portion 2169 forming an integral tab 2172, and a distal end of a pull wire 2174 is coupled to an inner or interior surface of tab 2172. Pull wire 2174 is an elongated element that passes through window 2165 of shaft component 2164 and runs or extends within lumen 2166 of shaft component 2164 such that a proximal end thereof is attached to trigger 2163. Stated another way, pull wire 2174 passes through window 2165 of shaft component 2164 such that only distal portion is positioned exterior to shaft component 2164 and the remaining length of the pull wire is positioned within shaft component 2164. During delivery of kicker tool 2160, lever arm 2170 is in a delivery configuration in which lever arm 2170 including tab 2172 is straight and extends adjacent to or abuts against an outer surface of shaft component 2164 as shown in the top view of FIG. 21A. Stated another way, when lever arm 2170 is in a delivery configuration, the lever arm has a straightened profile that is flush against the outer surface of shaft component 2164.

Figure 22A:
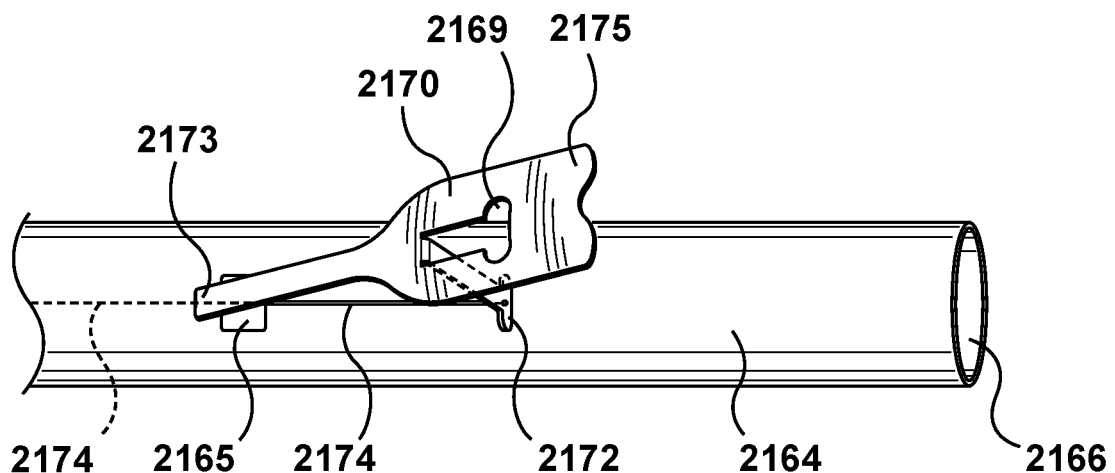
FIG. 22A is a top view illustration of a distal portion of the delivery system of FIG. 21A, wherein the lever arm is shown in a deployed or expanded configuration.

When it is desired to deploy or expand lever arm 2170, kicker tool 2160 is oriented or rotated around outer shaft 2106 in order to properly orient lever arm 2170 with respect to the target deployment site. Once positioned as desired, trigger 2163 of handle 2162 is operated by the user in order to pull or retract on pull wire 2174. With the distal end of pull wire 2174 attached or fixed to the inner surface of tab 2172 of lever arm 2170, tab 2172 bows or curves radially outward since proximal end 2173 of lever arm 2170 is also constrained or fixed to shaft component 2164. Second or distal end 2175 of lever arm 2170 is deflected or pushed radially outward to its deployed configuration as shown in FIG. 22 and FIG. 22A. More particularly, while proximal end 2173 of lever arm 2170 remains attached to the outer surface of shaft component 2164, distal end 2175 of lever arm 2170 expands or flares radially away from the outer surface of shaft component 2164 such that lever arm 2170 forms an acute angle between 0 and 90 degrees with respect to the outer surface of shaft component 2164. In the deployed or expanded configuration, lever arm 2170 has a curved configuration to apply a spring force against the vessel wall. Kicker tool 2160 and deployed lever arm 2170 do not move when distal capsule portion 2102 is retracted in order to deploy the prosthetic heart valve, thus ensuring that delivery system 2100 remains circumferentially centered within the native anatomy during deployment of the prosthetic heart valve. After the prosthetic heart valve is deployed as desired, in order to retract or recapture lever arm 2170, trigger 2163 is released in order to remove tension on pull wire 2174 and thereby collapse lever arm 2170 and/or permit the lever arm to return or revert to its delivery configuration. In another embodiment hereof, an outer sleeve or cover (not shown) may be distally advanced over the deployed lever arm in order to collapse and recapture the lever arm for removal.

Figure 21B:
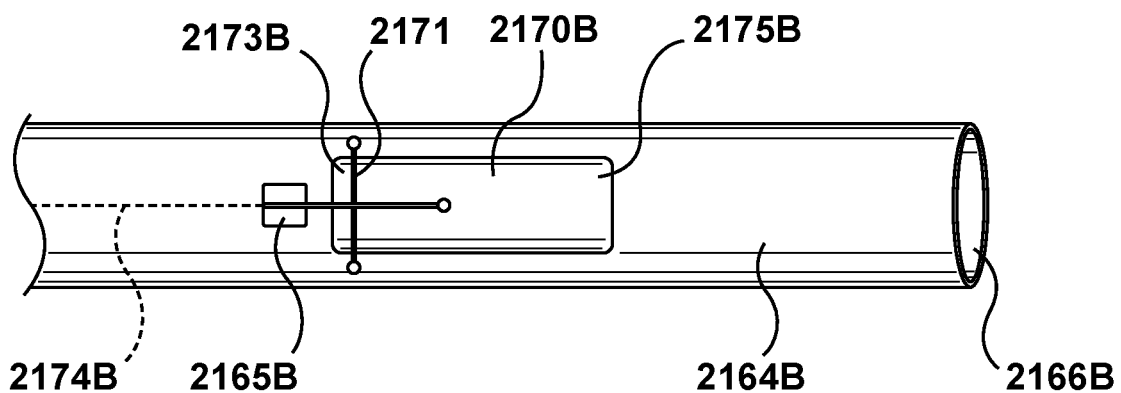
FIG. 21B is a top view illustration of a distal portion of a delivery system having a deployable lever arm according to an embodiment hereof, wherein the lever arm is shown in a delivery or unexpanded configuration.
Figure 22B:
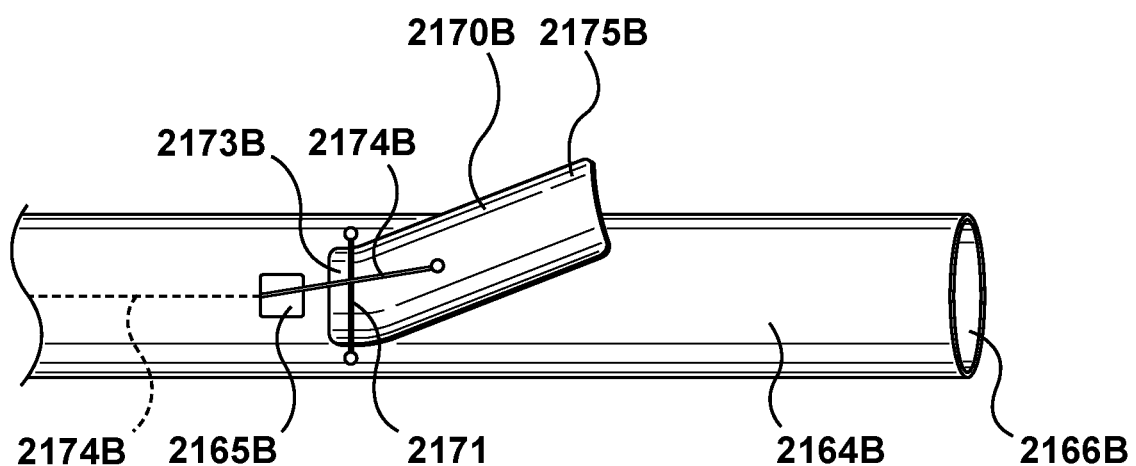
FIG. 22B is a top view illustration of a distal portion of the delivery system of FIG. 21B, wherein the lever arm is shown in a deployed or expanded configuration.

In another embodiment hereof as shown in FIG. 21B and FIG. 22B, the kicker tool includes a hinge 2171 in order to deploy a lever arm 2170B. Similar to lever arm 2170, lever arm 2170B is an individual or separate flat or ribbon-like element having a first or proximal end 2173B and a second or distal end 2175B. First or proximal end 2173B is fixed or attached to the exterior or outer surface of shaft component 2164B, while second or distal end 2175B is free or unattached to shaft component 2164B. Hinge 2171 is positioned on an exterior surface of shaft component 2164B and extends over proximal end 2173B of lever arm 2170B. A distal end of a pull wire 2174B is attached to an exterior surface of lever arm 2170B. Similar to pull wire 2174, pull wire 2174B is an elongated element that passes through window 2165B of shaft component 2164B and runs or extends within the lumen of shaft component 2164B such that a proximal end thereof is attached to a trigger (not shown in FIG. 21B and FIG. 22B). During delivery, lever arm 2170B is in a delivery configuration in which the lever arm is straight and extends adjacent to or abuts against an outer surface of shaft component 2164B as shown in the top view of FIG. 21B. Stated another way, when lever arm 2170B is in a delivery configuration, the lever arm has a straightened profile that is flush against the outer surface of shaft component 2164B.

When it is desired to deploy or expand lever arm 2170B, the trigger is operated by the user in order to pull or retract on pull wire 2174B. With the distal end of pull wire 2174B coupled to the exterior surface of lever arm 2170B, a second or unattached free end 2175B of lever arm 2170B is pulled proximally and radially outward since proximal end 2173B of lever arm 2170B is constrained or fixed to shaft component 2164B. Lever arm 2170B bends and deforms underneath hinge 2171 to permit second or distal end 2175B to flare or extend radially outward to its deployed configuration as shown in FIG. 22B. More particularly, while proximal end 2173B of lever arm 2170B remains attached to shaft component 2164B, distal end 2175B of lever arm 2170B expands or flares radially away from the outer surface of shaft component 2164B such that lever arm 2170B forms an acute angle with respect to the outer surface of shaft component 2164B. The kicker and deployed lever arm 2170B do not move when the prosthetic heart valve is deployed, thus ensuring that the delivery system remains circumferentially centered within the native anatomy during deployment of the prosthetic heart valve. After the prosthetic heart valve is deployed as desired, in order to retract or recapture lever arm 2170B, the trigger is released in order to remove tension on pull wire 2174B. Lever arm 2170B is formed from a self-expanding material such as Nitinol and shape-set in the delivery configuration shown in FIG. 21B. Thus, when tension is removed from pull wire 2174B, lever arm 2170B collapses and/or is permitted to return or revert to its straightened, delivery configuration. In another embodiment hereof, an outer sleeve or cover (not shown) may be distally advanced over the deployed lever arm in order to collapse and recapture the lever arm for removal.

Figures 23, 23A:
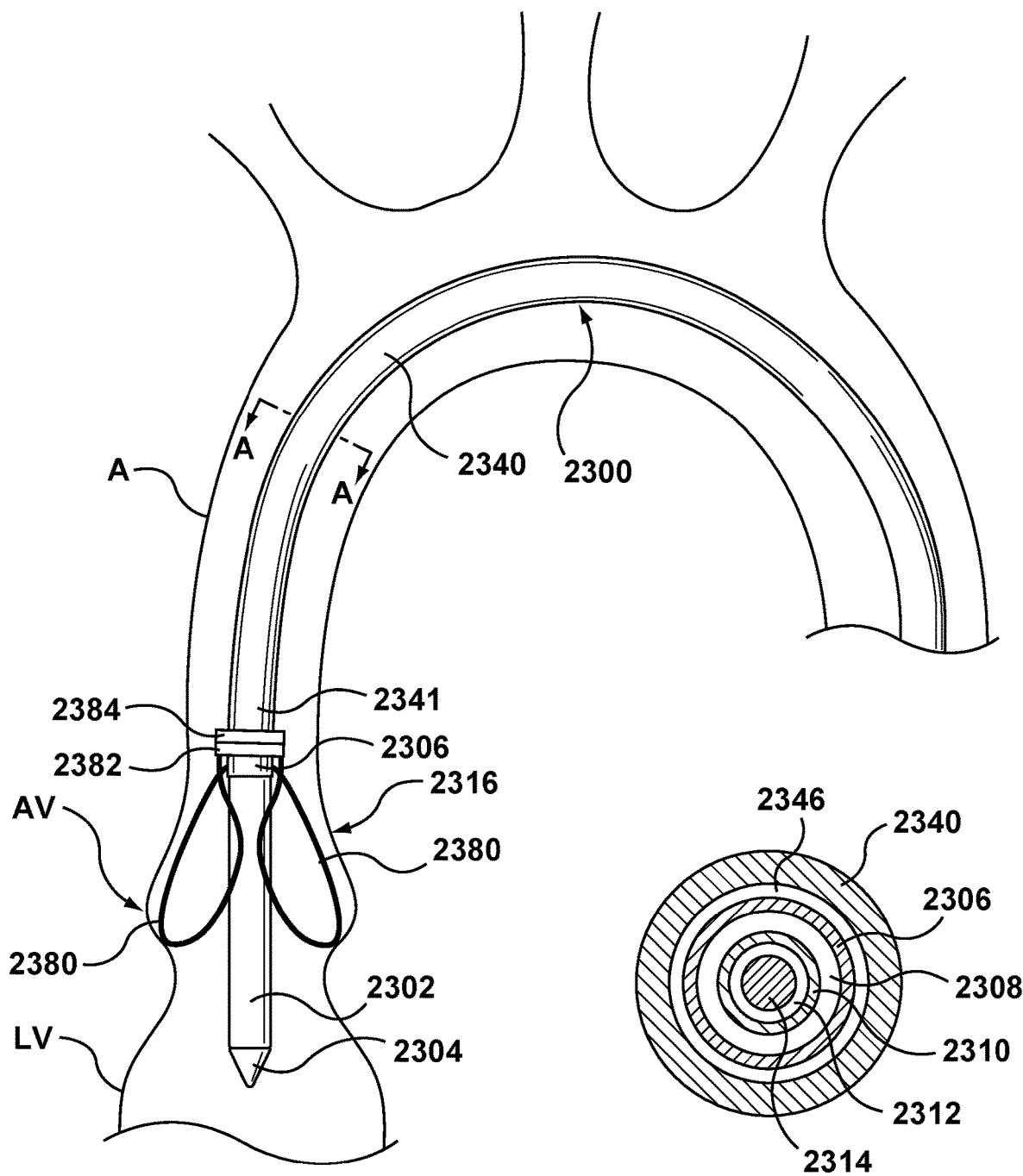
FIG. 23 is an illustration of a delivery system having an integral centering mechanism according to another embodiment hereof in situ, wherein the centering mechanism includes a plurality of deployable loops and is shown in a deployed or expanded configuration.
FIG. 23A is a cross-sectional view taken along line A-A of FIG. 23.

FIGS. 23-28 illustrate another embodiment hereof in which the centering mechanism includes a plurality of deployable loops that may be selectively deployed at or adjacent to the native valve annulus. In FIG. 23, a delivery system 2300 is depicted in situ, with centering mechanism 2316 in a deployed or expanded configuration and a prosthetic heart valve (not shown) in a delivery or compressed configuration in which the prosthetic heart valve is loaded within a distal capsule section 2302 of the delivery system. In this embodiment, centering mechanism 2316 includes a plurality of deployable loops 2380 that may be deployed within the cusps of the aortic annulus to center distal capsule portion 2302 of the delivery system within the native valve annulus for a more successful prosthetic valve deployment. Although centering mechanism 2316 is shown with three deployable loops 2380, centering mechanism 2316 may include a greater number of deployable loops or a fewer number of deployable loops, depending upon application.

In this embodiment, with reference to the cross-sectional view of FIG. 23A, in addition to an outer shaft 2306 that defines a lumen 2308 and an inner shaft 2310 that defines a lumen 2312 for receiving a guidewire 2314, delivery system 2300 includes an additional concentric outermost shaft 2340. Outer shaft 2306 is positioned within a lumen 2346 defined by outermost shaft 2340. Outermost shaft 2340 is shorter than outer shaft 2306, with a distal end 2341 positioned proximal to a proximal end of distal capsule portion 2302. In an embodiment hereof, distal end 2341 is positioned between 6-8 cm from a distal end 2304 of delivery system 2300 to permit retraction of distal capsule portion 2302. Outermost shaft 2340 includes a proximal hub 2384 mounted or attached to distal end 2341 thereof, and outer shaft 2306 includes a distal hub 2382 coupled to an outer surface thereof and positioned proximal to a proximal end of distal capsule portion 2302. Outer and outermost shafts 2306, 2340 operate independently such that distal and proximal hubs 2382, 2384, respectively, can be independently rotated or translated longitudinally relative to one another.

As will be explained in more detail herein, deployable loops 2380 are straight during advancement of delivery system 2300 into the anatomy and then are formed into their deployed or expanded in situ by simultaneous rotation and translational displacement thereof. Loops 2380 are individual or separate strands that extend between proximal and distal hubs 2384, 2382, respectively, with opposing ends of each loop 2380 being attached or fixed to one of the hubs. The three deployable loops 2380 are circumferentially spaced apart at approximately 120 degree intervals around outer shaft 2306. In an embodiment, each loop 2380 is initially formed or provided in a straight or delivery configuration as shown and described with respect to FIG. 24. Stated another way, the low energy configuration of each loop 2380 is the straight or delivery configuration of FIG. 24. Once loops 2380 are deployed, a locking or retention mechanism (not shown) may be utilized to maintain the deployed shape thereof until the loops are collapsed for recapture and removal. In another embodiment, each loop 2380 is formed from a self-expanding material such as Nitinol and shape-set in the deployed or expanded configuration shown in FIG. 23. Stated another way, in this alternative embodiment, the low energy configuration of each loop 2380 is the deployed or expanded configuration shown in FIG. 23. When loops 2380 are straightened for delivery, a locking or retention mechanism (not shown) may be utilized to maintain the delivery shape thereof until the loops are released for deployment. For example, the locking mechanism may be positioned in the handle. In another example, the locking mechanism may include a magnetic element or latch and release element disposed between proximal and distal hubs 2384, 2382.

Deployable loops 2380 are integral to delivery system 2300, with the prosthetic heart valve (not shown) being housed within distal capsule section 2302 which is distal to distal hub 2382 of outer shaft 2306. The addition of deployable loops 2380 to the profile of the delivery system is minimized because deployable loops 2380 are straightened and flush with the delivery system during delivery and also because deployable loops 2380 are positioned proximal to the prosthetic heart valve rather than stacked or in parallel with the prosthetic heart valve. Once delivery system 2300 is position as desired, but prior to deployment of the prosthetic heart valve, deployable loops 2380 may be deployed and then positioned in the coronary cusps to provide anatomical and accurate positioning of delivery system 2300 prior to deployment of the prosthetic heart valve. In particular, since deployable loops 2380 are positioned in the coronary cusps, centering mechanism 2316 provides both depth control as well as rotational alignment in order to properly position delivery system 2300. The deployment of loops 2380 are described in more detail with respect to FIGS. 24-28.

Figure 24:
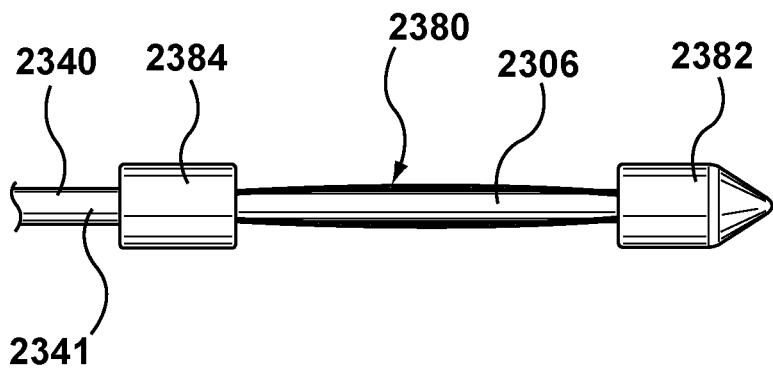
FIG. 24 is a side view of a portion of an outer shaft, an outermost shaft, and the plurality of loops of FIG. 23, with the components being shown removed from the delivery system of FIG. 23 for illustration purposes only, wherein the loops are shown in a straightened or delivery configuration.
Figure 25:
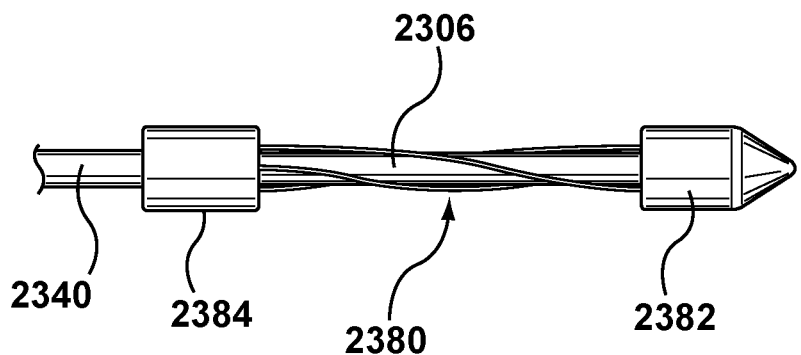
FIG. 25 is a side view of the components of FIG. 24 after relative rotation thereof.
Figure 26:
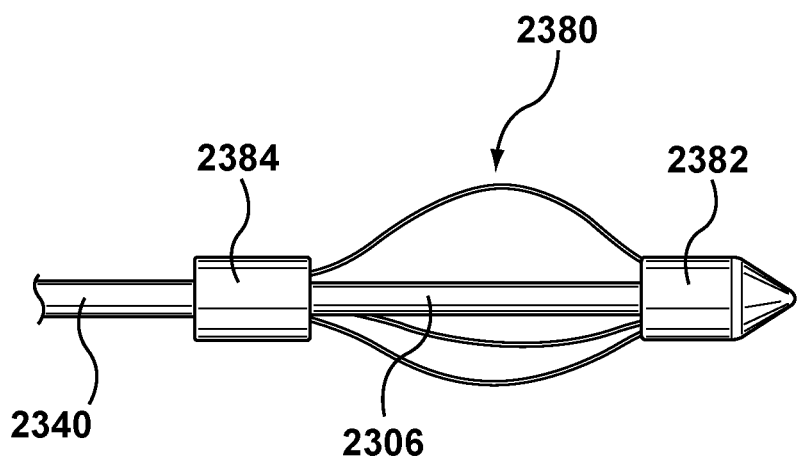
FIG. 26 is a side view of the components of FIG. 24 after relative longitudinal movement thereof.
Figure 27:
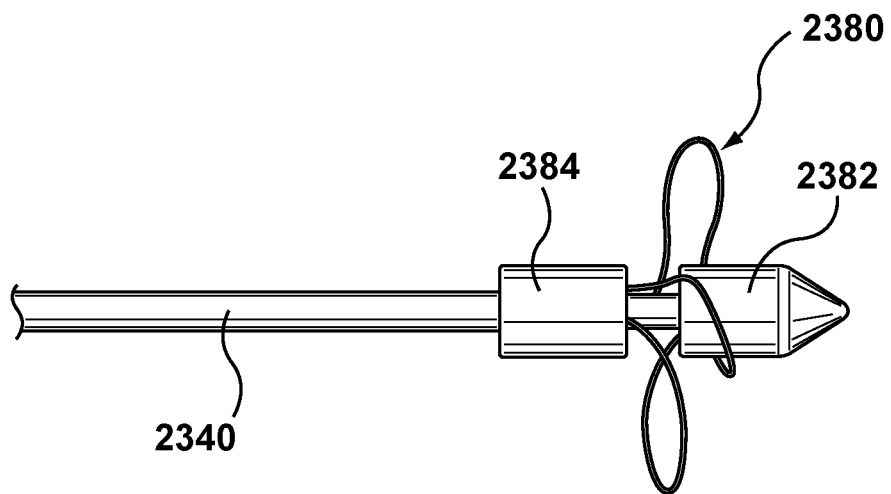
FIG. 27 is a side view of the components of FIG. 24 after simultaneous rotation and longitudinal movement thereof.

More particularly, FIG. 24 is a side view of a portion of outer shaft 2306, outermost shaft 2340, and loops 2380, with the components being shown removed from delivery system 2300 for illustration purposes only. During delivery, loops 2380 are substantially straight and extend between proximal and distal hubs 2384, 2382. Stated another way, when each loop 2380 is in a delivery configuration, the loop has a straightened profile that is flush against the outer surface of outer shaft 2306. When/if proximal and distal hubs 2384, 2382 are rotated with respect to each other, loops 2380 twist or spiral around outer shaft 2306 as shown in FIG. 25. When/if proximal and distal hubs 2384, 2382 are translated or moved longitudinally closer to each other, loops 2380 bulge or bow radially outwards away from outer shaft 2306 as shown in FIG. 26.

Figure 28:
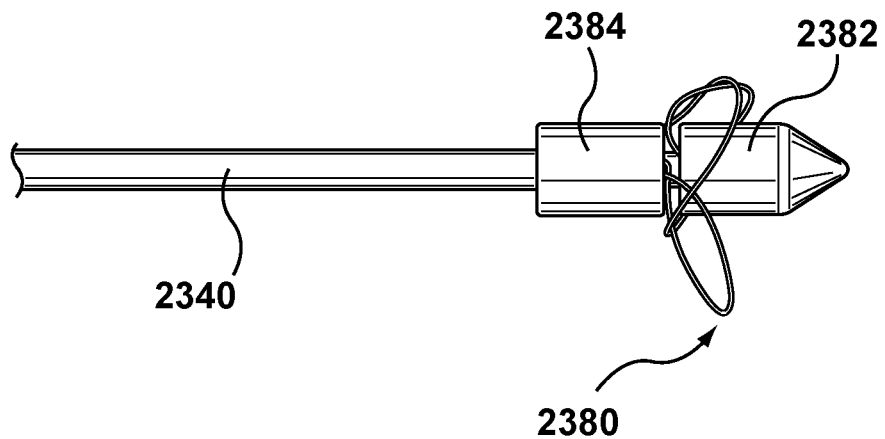
FIG. 28 is a side view of the components of FIG. 24 after further or additional simultaneous rotation and longitudinal movement thereof.

In order to achieve the deployed configuration of loops 2380, proximal and distal hubs 2384, 2382 are simultaneously rotated with respect to each other and translated or moved longitudinally closer to each other. More particularly, with reference to FIG. 27, proximal and distal hubs 2384, 2382 are simultaneously rotated and moved closer together in order to result in a propeller-like formation or configuration of loops 2380 in which loops 2380 both bulge or bow radially outwards away from outer shaft 2306 and also are twisted or spiral around outer shaft 2306. Additional rotation and translation result in loops 2380 bending or curving radially inwards and in a distal direction towards distal hub 2382 as shown in FIG. 28. With loops 2380 extending radially inwards and in a distal direction towards distal hub 2382, loops 2380 may be positioned in the coronary cusps to provide anatomical and accurate positioning of delivery system 2300 prior to deployment of the prosthetic heart valve. Thus, when each loop 2380 is in an expanded configuration, each loop 2380 has a curved, bowed profile radially spaced apart from the outer surface of outer shaft 2306 and each loop 2380 also spirals with respect to outer shaft 2380.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery system for a valve prosthesis configured for delivery within a vasculature, the delivery system comprising:
   an outermost shaft defining a central lumen and defining a plurality of lumens in a sidewall thereof;
   an outer shaft disposed within the central lumen of the outermost shaft, the outer shaft defining a lumen and being movable with respect to the outermost shaft;
   an inner shaft disposed within the lumen of the outer shaft, the inner shaft having a distal portion being configured to receive the valve prosthesis thereon; and
   a centering mechanism integrated onto the outermost shaft, the centering mechanism having a delivery configuration and an expanded configuration configured to circumferentially center the delivery system and the valve prosthesis within a native valve annulus in situ, wherein the centering mechanism has a straightened profile when in the delivery configuration and the centering mechanism has a curved, bowed profile radially larger than the outermost shaft and distal to a distal end of the outermost shaft when in the expanded configuration, and wherein the centering mechanism includes a plurality of elongated filaments each slidingly positioned within the plurality of lumens of the outermost shaft.

2. The delivery system of claim 1, wherein the outermost shaft is shorter than the outer shaft and the distal end of the outermost shaft is positioned proximal to a distal end of the outer shaft when the centering mechanism is in the expanded configuration.

3. The delivery system of claim 1, wherein
   each elongated filament having at least a distal portion formed from a self-expanding material, wherein when each elongated filament is in the delivery configuration the distal portion of each elongated filament is enclosed within one of the lumens in the sidewall of the outermost shaft and when each elongated filament is in the expanded configuration the distal portion of each elongated filament extends out of the distal end of the outermost shaft.

4. The delivery system of claim 1, wherein
   a distal end of each elongated filament being attached to an outer surface of the outer shaft, wherein when each elongated filament is in the delivery configuration a distal portion of each elongated filament is flush against the outer surface of the outer shaft and when each elongated filament is in the expanded configuration the distal portion of each elongated filament has the curved, bowed profile.

5. The delivery system of claim 1, wherein the outer shaft is rotatable and slidable relative to the outermost shaft.

6. A delivery system for a valve prosthesis configured for delivery within a vasculature, the delivery system comprising:
an outermost shaft defining a central lumen and defining a plurality of lumens in a sidewall thereof;
an outer shaft disposed within the central lumen of the outermost shaft, the outer shaft defining a lumen and being movable with respect to the outermost shaft;
an inner shaft disposed within the lumen of the outer shaft, the inner shaft having a distal portion being configured to receive the valve prosthesis thereon; and
a centering mechanism integrated onto the outermost shaft, the centering mechanism having a delivery configuration and an expanded configuration configured to circumferentially center the delivery system and the valve prosthesis within a native valve annulus in situ, wherein the centering mechanism includes a plurality of elongated filaments slidingly positioned within the plurality of lumens of the outermost shaft, and wherein a distal portion of each elongated filament is enclosed within one of the lumens in the sidewall of the outermost shaft when the centering mechanism is in the delivery configuration and the distal portion of each elongated filament extends out of a distal end of the outermost shaft when the centering mechanism is in the expanded configuration.

7. The delivery system of claim 6, wherein the distal end of the outermost shaft is flared.

8. The delivery system of claim 6, wherein each elongated filament is individually deployable.

9. The delivery system of claim 6, wherein the distal portion of each elongated filament is more flexible than a proximal portion thereof.

10. The delivery system of claim 6, wherein the distal portion of each elongated filament has a curved, bowed profile radially larger than the outermost shaft and distal to the distal end of the outermost shaft when in the expanded configuration.

11. The delivery system of claim 10, wherein at least the distal portion of each elongated filament is formed from a self-expanding material.

12. The delivery system of claim 6, wherein the distal portion of each elongated filament curls radially outward and longitudinally in a proximal direction such that a distal end of each elongated filament contacts an outer surface of the outermost shaft when in the expanded configuration.

13. The delivery system of claim 6, wherein the outermost shaft is shorter than the outer shaft and the distal end of the outermost shaft is positioned proximal to a distal end of the outer shaft when the centering mechanism is in the expanded configuration.

14. The delivery system of claim 6, wherein the plurality of elongated filaments includes exactly eight filaments.

15. A delivery system for a valve prosthesis configured for delivery within a vasculature, the delivery system comprising:
an outer shaft defining a plurality of lumens in a sidewall thereof;
an inner shaft disposed within the outer shaft, the inner shaft having a distal portion being configured to receive the valve prosthesis thereon; and
a centering mechanism integrated onto the delivery system, the centering mechanism having a delivery configuration and an expanded configuration configured to circumferentially center the delivery system and the valve prosthesis within a native valve annulus in situ, wherein the centering mechanism has a straightened profile and is disposed within the outer shaft when in the delivery configuration and the centering mechanism has a curved, bowed profile radially spaced apart from an outer surface of the outer shaft when in the expanded configuration, and wherein the centering mechanism includes a plurality of elongated filaments each slidingly positioned within the plurality of lumens of the outer shaft.

* * * * *